US012773418B2

(12) United States Patent
Lisanti et al.

(10) Patent No.: US 12,773,418 B2
(45) Date of Patent: Oct. 27, 2026

(54) ALKYL-TPP COMPOUNDS FOR MITOCHONDRIA TARGETING AND ANTI-CANCER TREATMENTS

(71) Applicant: LUNELLA BIOTECH, INC., Ottawa (CA)

(72) Inventors: Michael P. Lisanti, Ottawa (CA); Federica Sotgia, Ottawa (CA)

(73) Assignee: LUNELLA BIOTECH, INC., Ontario (CA)

( * ) Notice: Subject to any disclaimer, the term of this patent is extended or adjusted under 35 U.S.C. 154(b) by 968 days.

(21) Appl. No.: 17/604,651

(22) PCT Filed: Apr. 16, 2020

(86) PCT No.: PCT/US2020/028414
§ 371 (c)(1),
(2) Date: Oct. 18, 2021

(87) PCT Pub. No.: WO2020/214754
PCT Pub. Date: Oct. 22, 2020

(65) Prior Publication Data
US 2022/0211728 A1 Jul. 7, 2022

Related U.S. Application Data

(60) Provisional application No. 62/842,893, filed on May 3, 2019, provisional application No. 62/834,932, filed on Apr. 16, 2019.

(51) Int. Cl.
*A61K 31/66* (2006.01)
*A61K 31/167* (2006.01)
(Continued)

(52) U.S. Cl.
CPC ........... *A61K 31/66* (2013.01); *A61K 31/167* (2013.01); *A61K 31/375* (2013.01);
(Continued)

(58) Field of Classification Search
CPC ............. A61K 2300/00; A61K 31/167; A61K 31/375; A61K 31/4375; A61K 31/609;
(Continued)

(56) References Cited

U.S. PATENT DOCUMENTS

| | | | |
|---|---|---|---|
| 9,694,021 | B2 | 7/2017 | Chowhan et al. |
| 2014/0228290 | A1 | 8/2014 | Spitz et al. |

(Continued)

FOREIGN PATENT DOCUMENTS

| | | |
|---|---|---|
| EP | 3 124 027 A1 | 2/2017 |
| WO | 2013/019975 | 2/2013 |

(Continued)

OTHER PUBLICATIONS

De Francesco et al., Vitamin C and Doxycycline: A synthetic lethal combination therapy targeting metabolic flexibility in cancer stem cells (CSCs), Oncotarget, vol. 8, No. 40, 67269-67286, published Jun. 9, 2017 (Year: 2017).*

(Continued)

*Primary Examiner* — Sarah Pihonak
*Assistant Examiner* — Padmaja S Rao
(74) *Attorney, Agent, or Firm* — Nixon & Vanderhye, P.C.

(57) ABSTRACT

Alkyl-triphenylphosphonium compounds having a saturated, linear alkyl chain of about 9 to about 18 carbons may be used as therapeutic agents to treat cancer. Demonstrative compound dodecyl-TPP (d-TPP) dose-dependently inhibits the propagation of breast cancer stem cells and targets the adherent "bulk" of cancer cells, by decreasing MCF-7 cell viability. Further, d-TPP potently inhibits mitochondrial oxygen consumption rate, while simultaneously shifting cell metabolism toward the glycolytic pathway. This shift to a strict metabolic dependency on glycolysis may be used to eradicate the residual glycolytic CSC population, by using (Continued)

additional metabolic stressors. For example, d-TPP may be combined with a glycolytic inhibitor or an OXPHOS inhibitor, through co-administration or sequential administration, to treat cancer and eradicate CSCs.

30 Claims, 18 Drawing Sheets

(51) Int. Cl.

| | |
|---|---|
| ***A61K 31/375*** | (2006.01) |
| ***A61K 31/4375*** | (2006.01) |
| ***A61K 31/65*** | (2006.01) |
| ***A61K 31/7004*** | (2006.01) |
| ***A61K 31/7048*** | (2006.01) |
| ***A61K 31/7052*** | (2006.01) |

(52) U.S. Cl.
CPC .......... *A61K 31/4375* (2013.01); *A61K 31/65* (2013.01); *A61K 31/7004* (2013.01); *A61K 31/7048* (2013.01); *A61K 31/7052* (2013.01)

(58) Field of Classification Search
CPC .... A61K 31/65; A61K 31/66; A61K 31/7004; A61K 31/7052; A61K 45/06; A61K 31/662; A61K 31/7048; A61P 35/00; A61P 35/02
See application file for complete search history.

(56) References Cited

U.S. PATENT DOCUMENTS

| | | | | |
|---|---|---|---|---|
| 2016/0075726 | A1 | 3/2016 | Neuzil et al. | |
| 2018/0214402 | A1 * | 8/2018 | Schultz ................ | A61K 31/192 |

FOREIGN PATENT DOCUMENTS

| | | |
|---|---|---|
| WO | 2014/124384 | 8/2014 |
| WO | 2018/170109 | 9/2018 |
| WO | 2018/193113 | 10/2018 |
| WO | 2018/193114 | 10/2018 |
| WO | WO 2018195434 A1 | 10/2018 |
| WO | 2018/213764 | 11/2018 |
| WO | 2019/104115 | 5/2019 |
| WO | WO 2021/048830 A1 | 3/2021 |

OTHER PUBLICATIONS

Chinese Decision of Rejection for Chinese Application No. 2020800439794 issued Jul. 17, 2024.

F. F. Severin et al.: “Penetrating cation/fatty acid anion pair as a mitochondria-targeted protonophore”, Proceedings of the National Academy of Sciences, vol. 107, No. 2, Dec. 18, 2009, pp. 663-668, XP 055091441. *Abstract*.

De Francesco Ernestina Marianna et al: “Dodecyl-TPP Targets Mitochondria and Potently Eradicates Cancer Stem Cells (CSCs): Synergy With FDA-Approved Drugs and Natural Compounds (Vitamin C and Berberine)”, Frontiers in Oncology, vol. 9, Aug. 7, 2019, XP 093007323. *the whole document*

International Search Report and Written Opinion for PCT/US2020/028414 dated Sep. 3, 2020, 35 pages.

Sotgia, et al., A mitochondrial based oncology platform for targeting cancer stem cells (CSCs): MITO-ONC-RX, Cell Cycle, 2018, vol. 17:17, pp. 2091-2100.

Fajiu Li et al., “Azithromycin Effectively Inhibits Tumor Angiogenesis By Suppressing Vascular Endothelial Growth Factor Receptor 2-Mediated Signaling Pathways In Lung Cancer”, Oncology Letters, vol. 14: pp. 89-96, 2017.

* cited by examiner

A

B

MCF7 (24h)

h-TERT BJ1 (24h)

MCF7 (48h)

h-TERT BJ1 (48h)

ALKYL-TPP COMPOUNDS FOR MITOCHONDRIA TARGETING AND ANTI-CANCER TREATMENTS

RELATED APPLICATIONS

This application is the U.S. national phase of International Application No. PCT/US2020/028414 filed Apr. 16, 2020 which designated the U.S. and claims priority to U.S. Provisional Patent Application No. 62/834,932 filed Apr. 16, 2019, and U.S. Provisional Patent Application 62/842,893, filed May 3, 2019, the entire contents of each of which are hereby incorporated by reference.

FIELD

The present disclosure relates to inhibiting mitochondrial function and eradicating cancer, and in particular cancer stem cells (CSCs), using alkyl-triphenylphosphonium compounds, such as dodecyl-TPP.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis.

Mitochondria are extremely dynamic organelles in constant division, elongation and connection to each other to form tubular networks or fragmented granules in order to satisfy the requirements of the cell and adapt to the cellular microenvironment. The balance of mitochondrial fusion and fission dictates the morphology, abundance, function and spatial distribution of mitochondria, therefore influencing a plethora of mitochondrial-dependent vital biological processes such as ATP production, mitophagy, apoptosis, and calcium homeostasis. In turn, mitochondrial dynamics can be regulated by mitochondrial metabolism, respiration and oxidative stress. Thus, it is not surprising that an imbalance of fission and fusion activities has a negative impact on several pathological conditions, including cancer. Cancer cells often exhibit fragmented mitochondria, and enhanced fission or reduced fusion is often associated with cancer, although a comprehensive mechanistic understanding on how mitochondrial dynamics affects tumorigenesis is still needed.

An intact and enhanced metabolic function is necessary to support the elevated bioenergetic and biosynthetic demands of cancer cells, particularly as they move toward tumor growth and metastatic dissemination. Not surprisingly, mitochondria-dependent metabolic pathways provide an essential biochemical platform for cancer cells, by extracting energy from several fuels sources.

Recently, energetic metabolism and mitochondrial function have been linked to certain dynamics involved in the maintenance and propagation of CSCs, which are a distinguished cell sub-population within the tumor mass involved in tumor initiation, metastatic spread and resistance to anti-cancer therapies. For instance, CSCs show a peculiar and unique increase in mitochondrial mass, as well as enhanced mitochondrial biogenesis and higher activation of mitochondrial protein translation. These behaviors suggest a strict reliance on mitochondrial function. Consistent with these observations, an elevated mitochondrial metabolic function and OXPHOS have been detected in CSCs across multiple tumor types. Likewise, the fluorescent mitochondrial dye MitoTracker has been used to enrich and purify CSCs. The dye accumulates in CSCs, and allows for characterizing cancer cell sub-populations based on degrees of anchorage-independent growth in vitro and higher tumor-initiating capability in vivo. Adding to this, during asymmetric cell division younger mitochondria are clustered within daughter cells that retain stem-like phenotype, whereas daughter cells committed to differentiation lose stem traits and receive more aged mitochondria, further supporting the idea that the most functionally intact, viable and undamaged mitochondria are selected for supporting sternness.

Based on these observations, novel pharmacological approaches aimed at targeting mitochondria in CSCs have been proposed, some of which have also been successfully applied in pre-clinical and clinical studies. For instance, the antibiotic Doxycycline, which decreases mitochondrial protein translation as an off-target effect, has been suggested for repurposing in the clinical management of early breast cancer patients for its ability to selectively target CSCs. What is needed, then, is the identification of candidate cancer therapeutic compounds that target and inhibit mitochondrial function.

However, certain limitations restrain the use of sole anti-mitochondria agents in cancer therapy, as adaptive mechanisms can be adopted in the tumor mass to overcome the lack of mitochondrial function. These adaptive mechanisms include, for example, the ability of CSCs to shift from oxidative metabolism to alternate energetic pathways, in a multi-directional process of metabolic plasticity driven by both intrinsic and extrinsic factors within the tumor cells, as well as in the surrounding niche. Notably, in CSCs the manipulation of such metabolic flexibility can turn as advantageous in a therapeutic perspective. What is needed, then are therapeutic approaches that either prevent these metabolic shifts, or otherwise take advantage of the shift to inhibit cancer cell proliferation.

An objective of this disclosure is to identify and describe new therapeutic compounds that target and inhibit mitochondrial function, and may serve as anti-cancer therapeutics. Another object of this disclosure is to identify and describe new therapeutic approaches using such therapeutic compounds that prevent cancer cell metabolic shifts, and/or take advantage of the metabolic shift to inhibit cancer cell proliferation and eradicate CSCs.

SUMMARY

Elevated mitochondrial metabolism is a distinguishing feature of cancer stem cells (CSCs), which are involved in tumor initiation, dissemination at secondary sites, as well as therapy resistance. Mitochondria-impairing agents can be used to efficiently hamper CSC maintenance and propagation toward a better control of the neoplastic disease. Triphenylphosphonium (TPP)-based mitochondria-targeted compounds are small, generally non-toxic, and biologically active molecules that accumulate in mitochondria of living cells, and represent candidates for anti-cancer therapies to block CSC growth and proliferation.

Described herein are cancer therapies utilizing the selective mitochondrial inhibition properties of novel alkyl-triphenylphosphonium compounds (A-TPP), such as dodecyl-TPP (d-TPP). It should be appreciated that A-TPP compounds are cations, normally available as salts (e.g., d-TPP bromide). Embodiments of the present approach may take the form of pharmaceutical compositions including a pharmaceutically effective amount of an A-TPP compound, such as d-TPP, as well as methods of treating cancer, inhibiting cancer growth, eradicating CSCs, preventing or reducing the likelihood of tumor recurrence, and preventing or reducing the likelihood of metastasis. In some embodiments, an A-TPP compound such as d-TPP may be used as a first metabolic inhibitor in combination with a second metabolic inhibitor that impedes glycolysis and/or OXPHOS. Such combinations may be used as anti-cancer therapies to treat cancer, inhibit cancer growth, eradicate CSCs, prevent or reduce the likelihood of tumor recurrence, and prevent or reduce the likelihood of metastasis.

This disclosure relates to compositions and therapeutic strategies involving d-TPP, which is twice as potent as other TPP-derivative compounds noted below, with respect to inhibiting CSC propagation. Advantageously, d-TPP targets the bulk of cancer cells, reducing their viability, but having a limited effect on normal fibroblasts. It is possible that in cancer cells and CSCs in particular, the mitochondrial membrane potential is higher than in normal or healthy cells. TPP-based strategies, then, may be used to distinguish between "normal" and "malignant" mitochondria, mainly on the basis of the intrinsic chemical-physical characteristics of these organelles in health and disease. Of note, d-TPP treatment determined a shift in energetic metabolism toward the activation of the glycolytic pathway, which is very likely boosted as a compensatory response to the anti-mitochondrial effect elicited by d-TPP. This metabolic shift has unveiled a strict dependency of cancer cells on glycolysis after d-TPP treatment. In CSCs the manipulation of such metabolic flexibility can turn as advantageous in a therapeutic perspective. For instance, synchronizing CSCs toward certain metabolic dependencies thus blocking their ability to shift among several energetic pathways, may represent a useful strategy toward CSCs eradication. Consequently, the present approach includes therapeutic "two-hit" strategies involving the use of a second metabolic inhibitor (glycolysis or OXPHOS) to further starve the residual CSCs population.

In embodiments of the "two-hit" strategies of the present approach, an A-TPP compound, such as d-TPP, is used as a first metabolic inhibitor to impair CSC mitochondria and cause cancer cells to shift towards a glycolytic state. This is followed by the use of a second metabolic inhibitor (glycolysis or OXPHOS) that deprives cancer cells of a viable energy source, inhibiting propagation, recurrence, and metastasis. It should be appreciated that the metabolic inhibitors may be administered simultaneously, or sequentially. For example, d-TPP may be administered first, to cause the metabolic shift in CSCs towards glycolysis, and then the second metabolic inhibitor may be administered.

The metabolic and biological effects induced by d-TPP on cancer cells, and in particular breast cancer cells, are described below. The 3D mammosphere assay in MCF-7 cells was used to demonstrate that treatment with d-TPP dose-dependently inhibits the propagation of breast CSCs in suspension. Also, the results show that d-TPP targets the adherent "bulk" of cancer cells, by decreasing MCF-7 cell viability. The analysis of metabolic flux using Seahorse Xfe96 shows that d-TPP potently inhibits mitochondrial oxygen consumption rate, while simultaneously shifting cell metabolism toward the glycolytic pathway.

After this metabolic shift, CSC dependency on glycolysis may be used to eradicate the residual glycolytic CSC population through additional metabolic stressors. Demonstrative combinations of d-TPP and second metabolic inhibitors were used to validate the "two-hit" therapeutic strategy of the present approach. The selected second metabolic inhibitors included natural and synthetic compounds, some of which are FDA-approved, known to behave as glycolysis inhibitors (e.g., Vitamin C, 2-Deoxy-Glucose or 2DG) or OXPHOS inhibitors (e.g., Doxycycline, Niclosamide, Berberine Chloride) inhibitors. Embodiments of the "two-hit" therapeutic strategy effectively decreased CSC propagation, at concentrations of d-TPP toxic only to cancer cells, but not to normal cells. Toxicity was evaluated using normal human fibroblasts (hTERT-BJ1) and the chick chorioallantoic membrane assay.

The results disclosed herein demonstrate that d-TPP halts CSC propagation and targets the bulk of cancer cells, without eliciting relevant undesirable off-target effects in normal cells. These observations pave the way for further exploring the potential of TPP-based derivatives in cancer therapy. Moreover, TPP-based compounds should be investigated for their potential to discriminate between "normal" and "malignant" mitochondria, suggesting that distinct biochemical and metabolic changes in these organelles could precede specific normal or pathological phenotypes. Lastly, the data validate that the manipulation of the energetic machinery represents a useful tool to control stem traits in cancer cells.

Under the present approach, pharmaceutical compositions may include a pharmaceutically effective amount of an A-TPP compound, such as d-TPP, which includes pharmaceutically acceptable salts thereof, and a pharmaceutically acceptable carrier, diluent, or excipient therefor. Some embodiments of the pharmaceutical composition may also include a pharmaceutically effective amount of a second metabolic inhibitor compound, such as a glycolysis inhibitor or an OXPHOS inhibitor. The second metabolic inhibitor compound may, in some embodiments, be in a separate pharmaceutically acceptable carrier. Compounds according to the present approach may be used as anti-cancer therapeutics. Pharmaceutically-effective amounts of compounds according to the present approach may be administered to a subject according to means known in the art. The d-TPP may be co-administered with a second metabolic inhibitor compound in some embodiments. Alternatively, d-TPP may be administered prior to, and optionally before and with, a second metabolic inhibitor. Compounds of the present approach may be administered to treat a cancer, to eradicate CSCs, to prevent or reduce the likelihood of tumor recurrence, and to prevent or reduce the likelihood of metastasis. In some embodiments, a pharmaceutically effective amount of d-TPP may be administered to cause a cancer to shift to a glycolytic state. In some embodiments, a pharmaceutically effective amount of d-TPP may be administered to increase the effectiveness of a chemotherapy. In some embodiments, a pharmaceutically effective amount of d-TPP may be administered to treat, prevent, and/or reduce the likelihood of at least one of tumor recurrence and metastasis, drug resistance, and radiotherapy resistance.

BRIEF DESCRIPTION OF THE DRAWINGS

FIG. 4A shows results after 24 hours, FIG. 4B shows results after 48 hours, and FIG. 4C shows results after 72 hours.

DESCRIPTION

Figure 1:
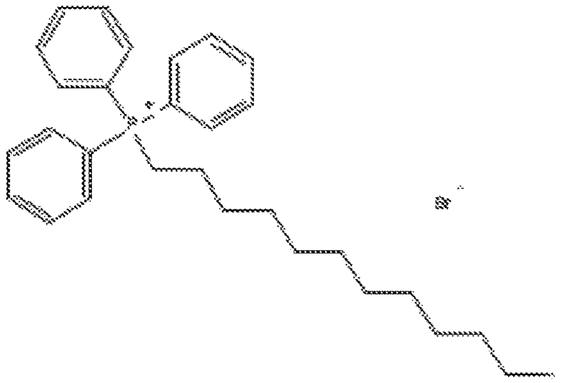
FIG. 1 shows the structures of d-TPP (structure A) and b-TPP (structure B).
Figure 1:
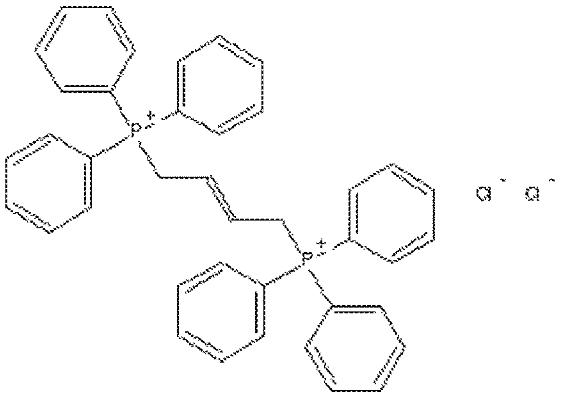

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

This description uses various terms that should be understood by those of an ordinary level of skill in the art. The following clarifications are made for the avoidance of doubt. The terms “treat,” “treated,” “treating,” and “treatment” include the diminishment or alleviation of at least one symptom associated or caused by the state, disorder or disease being treated, in particular, cancer. In certain embodiments, the treatment comprises diminishing and/or alleviating at least one symptom associated with or caused by the cancer being treated, by the compound of the invention. In some embodiments, the treatment comprises causing the death of a category of cells, such as CSCs, of a particular cancer in a host, and may be accomplished through preventing cancer cells from further propagation, and/or inhibiting CSC function through, for example, depriving such cells of mechanisms for generating energy. For example, treatment can be diminishment of one or several symptoms of a cancer, or complete eradication of a cancer.

The terms “cancer stem cell” and “CSC” refer to the subpopulation of cancer cells within tumors that have capabilities of self-renewal, differentiation, and tumorigenicity when transplanted into an animal host. Compared to “bulk” cancer cells, CSCs have increased mitochondrial mass, enhanced mitochondrial biogenesis, and higher activation of mitochondrial protein translation. As used herein, a “circulating tumor cell” is a cancer cell that has shed into the vasculature or lymphatics from a primary tumor and is carried around the body in the blood circulation. The CellSearch Circulating Tumor Cell Test may be used to detect circulating tumor cells.

The phrase “pharmaceutically effective amount,” as used herein, indicates an amount necessary to administer to a host, or to a cell, tissue, or organ of a host, to achieve a therapeutic result, such as regulating, modulating, or inhibiting protein kinase activity, e.g., inhibition of the activity of a protein kinase, or treatment of cancer. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

As used herein, the phrase “active compound” refers to the A-TPP compounds described herein, which may include a pharmaceutically acceptable salt or isotopic analog thereof. The phase “active compound” may also include any second inhibitor compound in embodiments having a second inhibitor, such as a glycolysis inhibitor or an OXPHOS inhibitor. It should be appreciated that the active compound(s) may be administered to the subject through any suitable approach, as would be known to those having an ordinary level of skill in the art. It should also be appreciated that the amount of active compound and the timing of its administration may be dependent on the individual subject being treated (e.g., the age and body mass, among other factors), on the manner of administration, on the pharmacokinetic properties of the particular active compound(s), and on the judgment of the prescribing physician. Thus, because of subject to subject variability, any dosages described herein are intended to be initial guidelines, and the physician can titrate doses of the compound to achieve the treatment that the physician considers appropriate for the subject. In considering the degree of treatment desired, the physician can balance a variety of factors such as age and weight of the subject, presence of preexisting disease, as well as presence of other diseases. Pharmaceutical formulations can be prepared for any desired route of administration including, but not limited to, oral, intravenous, or aerosol administration, as discussed in greater detail below.

Inter- and intra-tumor heterogeneity is one of the main factors accounting for tumor progression and therapy failure. CSCs originate and drive such heterogeneity, for their ability to give rise to a hierarchically differentiated progeny toward the generation of the full repertoire of cell types within the tumor mass. Thereafter, pharmacological strategies aimed at identifying and selectively targeting CSCs have been implemented among the most promising, though challenging approaches in a therapeutic perspective. Diverse theories have been proposed for the explanation of the origin of CSCs. According to the so-called “metabo-stemness” model, certain metabotypic phenotypes may dictate the stemness properties in tumors. This model suggests that specific metabolic dynamics may drive the acquisition of stem traits from non-cancer or differentiated cancer cells. Likewise, onco-metabolism has been included among the novel hallmarks of cancer. On the basis of these observations, it’s not surprising that cancer metabolism has been regarded as an opportunity to selectively target CSCs.

CSCs across diverse tumor types show peculiar metabolic features, including an increased OXPHOS capacity, an elevated mitochondrial biogenesis, and a higher mitochondrial mass compared to the non-stem cancer population. Corroborating these findings, cancer cells with higher telomerase (hTERT$^{high}$) activity and therefore higher immortality features, specifically exhibit an increased mitochondrial mass, compared to hTERT$^{low}$ counterpart. These observations suggest that mitochondria-impairing agents could be used to specifically inhibit the CSC population, paving the way for the identification of chemical strategies aimed at selectively targeting mitochondria in CSCs.

Mitochondrial inhibition is an effective strategy for inhibiting cancer recurrence and metastasis, and for eradicating cancer cells and CSCs in particular. For instance, the antibiotic Doxycycline behaves as a mitochondrial inhibitor that impairs CSC activity. Prolonged treatment with Doxycycline turns on the glycolytic pathway in CSCs, in response to the mitochondrial dysfunction. The use of a glycolysis inhibitor like Vitamin C in combination with Doxycycline can completely eradicate CSCs. The combination of Doxycycline and Vitamin C represents a safe approach for the clinical management of cancer patients. It is well-known that Doxycycline has a very manageable spectrum of side effects at biologically active concentrations, and that Vitamin C has potentially no side effects. Adding to this, data from meta-analysis of 21 published studies, as well as pre-clinical investigations, have demonstrated that oral doses of vitamin C reduce cancer risk, overall mortality and disease-specific mortality in lung and breast cancer. Furthermore, a one-week oral administration of ascorbate performed before cell inoculation has decreased tumor development in a lymphoma xenograft model.

Clinical validation of these findings for Doxycycline has been provided in a recent pilot study organized by the inventors. In this study, early breast cancer patients were enrolled for a short-term (14 days) pre-operative Doxycycline administration. Notably, the analysis of post-operative vs pre-operative breast tumor specimens showed a selective reduction in the stem markers CD44 and ALDH in the patients receiving Doxycycline compared to controls, providing clinical evidence that mitochondria-targeting strategies may be used to efficiently halt CSC propagation; nevertheless, additional studies are necessary to investigate the action of Doxycycline together with Vitamin C in breast cancer patients.

Tri-phenyl-phosphonium (TPP) is an example of a lipophilic cation that targets cellular mitochondria. The TPP moiety may be covalently linked to a therapeutic compound, and deliver the linked therapeutic compound to mitochondria. Generally, the therapeutic compound will be present in mitochondria at higher concentrations than elsewhere in the cell. The inventors established that some compounds carrying the TPP moiety inhibit mitochondrial function and therefore reduce CSC propagation. The TPP moiety, which acts as a mitochondrial targeting signal, may be chemically attached to a “cargo” therapeutic compound molecule via a covalent bond. The intrinsic nature of the cargo molecule and its binding to the TPP structure may deeply influence the accumulation of the therapeutic compound in the mitochondria of living cells, thereafter impacting its overall biological function.

The covalent modification of a compound to a TPP cation is thus a method to deliver probes and imaging agents to mitochondria. TPP$^+$ cations may serve as very efficient chemical “vehicles” to transport small molecules to the mitochondria. In addition, their chemical synthesis is easily achievable, and the degree of accumulation in the mitochondria is elevated, because of the chemical attraction between the positively charged TPP cation and the negative membrane potential of the mitochondrial inner membrane.

Certain chemical derivatives of TPP also target mitochondria and possess mitochondrial inhibition activity, and thus are useful for targeting and eradicating cancer cells. International patent application PCT/US2018/062174, filed Nov. 21, 2018 and incorporated by reference in its entirety, describes examples of TPP-derivatives having anti-cancer activity. For example, the inventors demonstrated that the TPP-derivative compound 2-butene-1,4-bis-TPP (b-TPP) impairs mitochondrial metabolic function leading to the inhibition of breast CSC activity.

Described herein are novel therapeutic approaches using an integrated metabolic strategy for eradicating CSCs, employing the advantageous properties of A-TPP compounds having between about 9 and about 18 carbons in the saturated, linear alkyl chain:

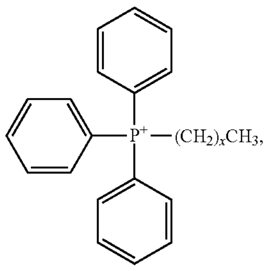

wherein ‘x’ is from 8 to 17, and preferably from 9 to 16, and more preferably from 11 to 14. In an illustrative embodiment, x is 11, resulting in d-TPP discussed in the examples below.

In the demonstrative embodiments of the present approach, the compound d-TPP is employed as a therapeutic agent that inhibits mitochondrial function in CSCs. It should be appreciated that other A-TPP compounds, having between about 9 and about 18 carbons in the alkyl chain, may be used without departing from the present approach. The mitochondrial inhibition effects of d-TPP, a compound that carries a mitochondria-targeting TPP moiety, result in a dose-dependent and time-dependent reduction in cell viability.

These effects reduce the formation of 3D mammospheres, assayed as a read-out for CSC activity. Metabolic flux analysis indicates that d-TPP potently inhibits mitochondrial basal respiration and ATP production. Combined, these effects provide a rationale for the reduction in CSC functional capability, as observed in response to the administration of d-TPP as described below. Breast cancer cells preferentially exhibit a glycolytic phenotype in response to d-TPP. This metabolic switch allows a subset of CSCs to cope with the anti-mitochondrial effects of d-TPP.

In some embodiments, the present approach targets this dependency through a "two-hit" combination of d-TPP and a second metabolic inhibitor (glycolysis or OXPHOS) to further starve the residual CSC population. The d-TPP compound is used as a first metabolic inhibitor (specifically, as a mitochondria impairing agent) that serves as first-hit, followed by the use of a second metabolic inhibitor (for instance a glycolysis or an OXPHOS inhibitor) that acts as a second-hit.

Despite the acquisition of this compensatory glycolytic behavior, d-TPP treatment weakens CSCs by rendering them more sensitive to the action of glycolytic inhibitors and OXPHOS inhibitors. Thus, the effects of d-TPP allow for a variety of combination therapies. Under the present approach, d-TPP may be administered with one or more of such inhibitors, providing a "two-hit" therapeutic approach to eradicating CSCs. Demonstrative examples of the second metabolic inhibitor include glycolysis inhibitors Vitamin C and 2-deoxy-D-glucose (2-DG), as well as the OXPHOS inhibitors Doxycycline, Azithromycin, Niclosamide, and Berberine Chloride. Other FDA-approved members of the tetracycline family, including, for example, Tetracycline, Chlortetracycline, Minocycline, and Tigecycline, or the erythromycin family, including, for example, Erythromycin, Telithromycin, Clarithromycin, and Roxithromycin, may be used without departing form the present approach, Eravacycline, Sarecycline, and Omadacycline. A functional validation of the present approach is provided below, in which the simultaneous treatment of MCF-7 cells with d-TPP and a second metabolic inhibitor resulted in an almost complete loss of CSCs activity.

As mentioned, some derivatives of the TPP moiety also have the potential to inhibit cancer growth and metastasis. Using an ATP depletion assay as a surrogate marker of mitochondrial dysfunction, the inventors identified several TPP-derivatives in International Application PCT/US2018/062174, filed Nov. 21, 2018 and incorporated by reference in its entirety. For example, the compound 2-butene-1,4-bis-TPP (b-TPP), showed considerable efficacy in inhibiting CSC propagation (IC-50~500 nM). The accumulation of the TPP-derivative in mitochondria, as well as the compound's mitochondrial inhibition and anti-cancer efficacy, heavily depend on the particular structure. What is needed are further TPP-derivative compounds having anti-cancer efficacy.

The inventors identified dodecyl-TPP as another TPP-derivative having considerable mitochondrial inhibition and anti-cancer efficacy. The metabolic and biological properties of the d-TPP compound are described below. In addition, combination strategies that efficiently target the plastic energetic cell machinery of CSCs and eradicate cancer are described below. The d-TPP structure, shown below, is an organo-phosphorous cation with a quaternary phosphate having three phenyl rings and a saturated, 12-carbon alkyl chain.

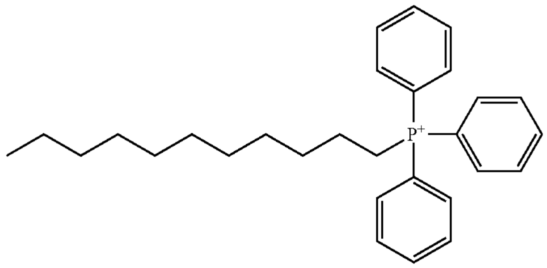 [SMILES: CCCCCCCCCCC[P+](c1ccccc1)(c1ccccc1)c1ccccc1]

As a cation, d-TPP may be a salt, such as a bromide salt. FIG. 1 compares d-TPP (structure A) as a bromide salt to 2-butene-1,4-bis-TPP (structure B). As can be seen, d-TPP has only one TPP moiety, and a long hydrophobic alkyl chain. B-TPP, on the other hand, has two TPP moieties linked by butene.

Figure 2:
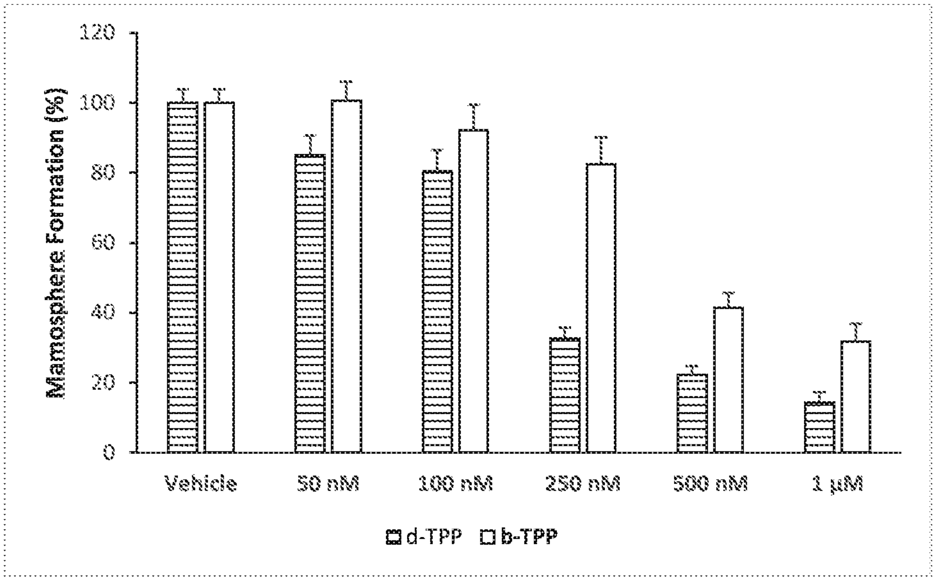
FIG. 2 shows results of the mammosphere assay on MCF-7 cells exposed to d-TPP and b-TPP at various concentrations.

Both d-TPP and b-TPP inhibit CSC propagation, but d-TPP is significantly more potent. The mammosphere formation assay was used as a read-out for CSC propagation, in Estrogen Receptor (ER)-positive MCF-7 breast cancer cells treated with increasing concentrations of d-TPP or b-TPP. The results are shown in FIG. 2, comparing the CSC propagation inhibition activities of d-TPP and b-TPP at the same concentrations. As shown in FIG. 2, the treatment with d-TPP resulted in an 80% reduction in CSC propagation at the highest concentrations tested (500 nM and 1 μM); a slight but significant reduction (20%) in mammosphere formation was already observed at very low concentrations (50 nM and 100 nM) for d-TPP. In comparison to b-TPP, d-TPP was more than twice as potent in terms of inhibiting mammosphere formation.

Figure 3:
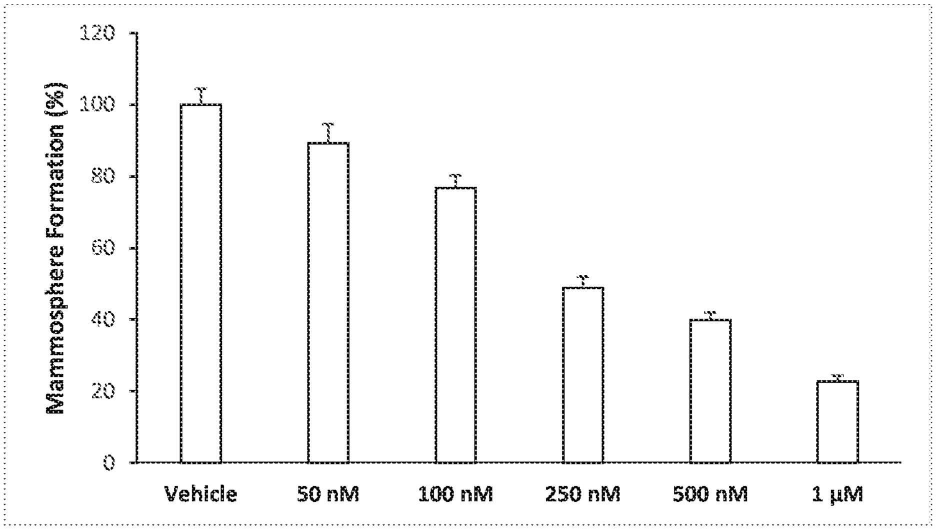
FIG. 3 shows results of the mammosphere assay on MDA-MB-231 cells exposed to d-TPP at various concentrations.

The inhibitory effect of d-TPP was also tested on triple negative breast cancer cells line MDA-MB-231. A similar inhibitory trend on CSC propagation was observed in the triple negative breast cancer cells line MDA-MB-231. The results of the mammosphere formation assay on MDA-MB-231 cells are shown in FIG. 3. As can be seen, d-TPP showed an inhibitory effect at the lowest concentration tested, 50 nM, and achieved similar inhibition at 1 μM, nearing 80%.

Figure 4A:
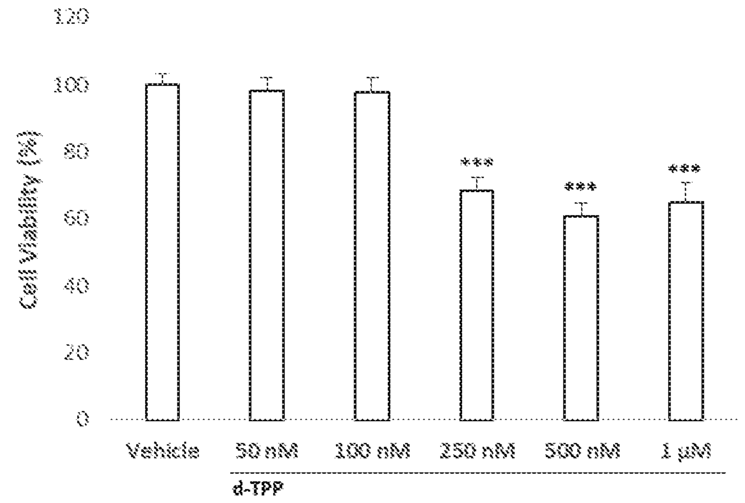
FIGS. 4A-4C compare the results of cell viability testing using different concentrations of d-TPP on MCF-7 breast cancer cells and h-TERT normal cells.
Figure 4A:
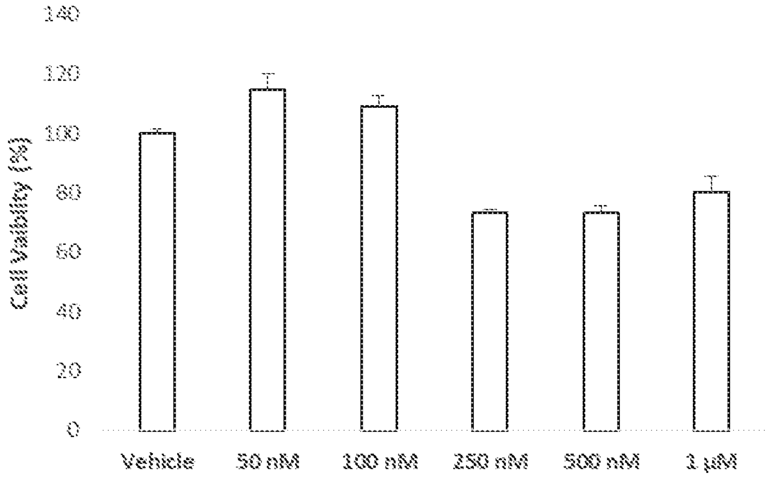
Figure 4B:
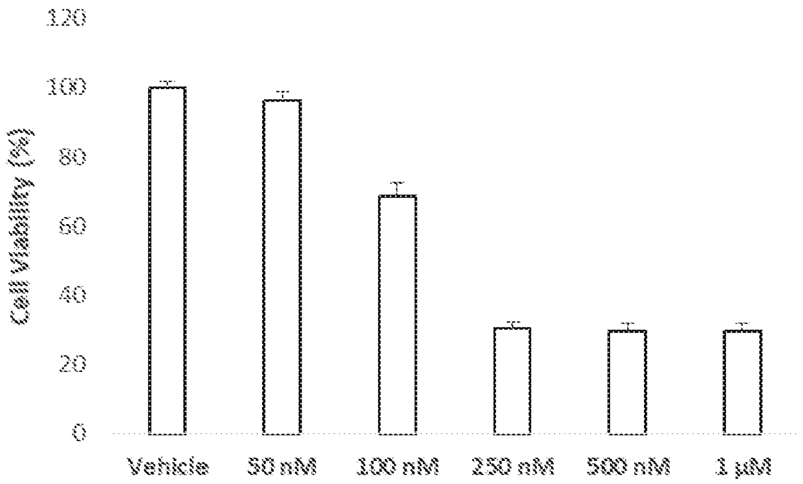
Figure 4B:
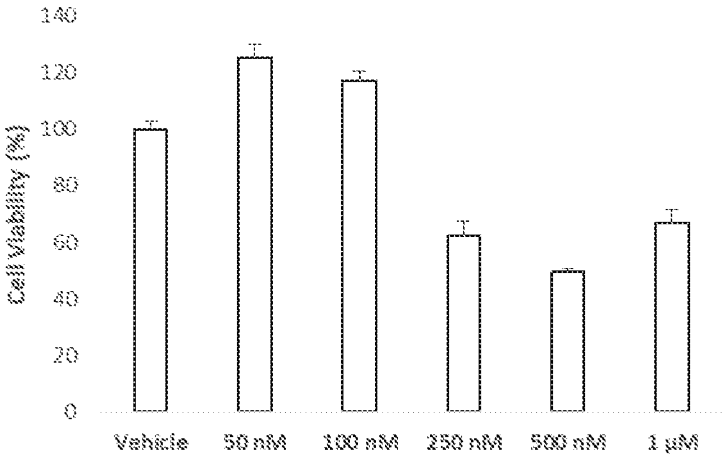
Figure 4C:
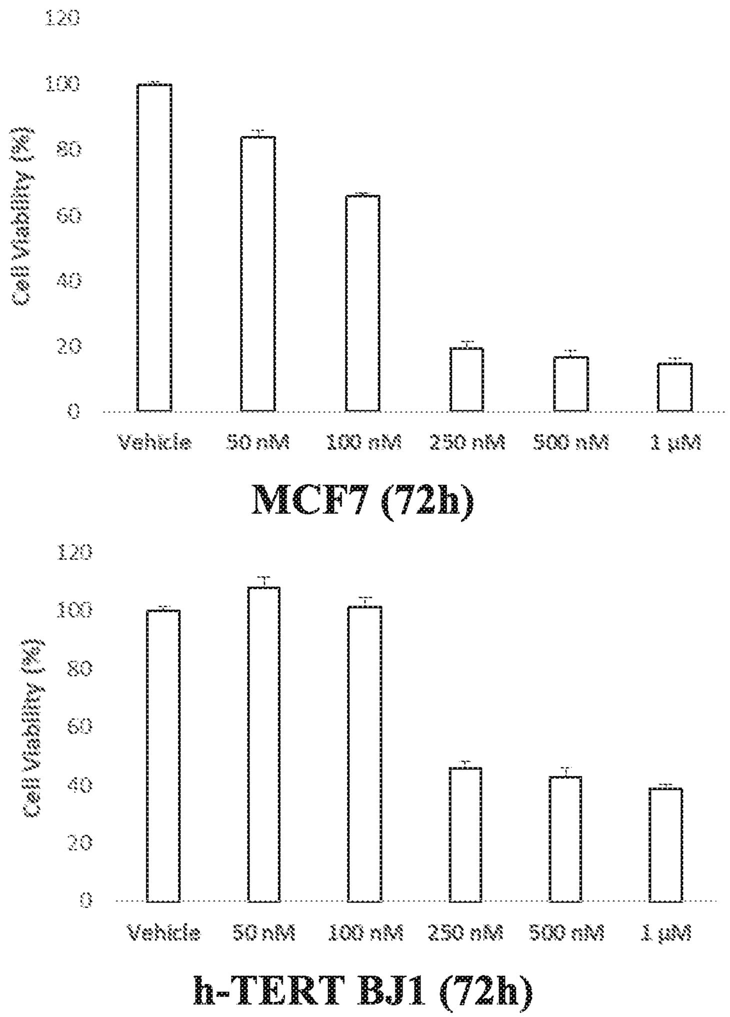

The inventors' prior efforts indicated that certain TPP-derivatives may interfere with mitochondrial function in cancer cells, impairing their metabolic activity and ultimately leading to a reduction in cancer cell viability. Of interest, these actions for certain TPP-compounds are selectively elicited on cancer cells, but not on normal (i.e., healthy) cells. To demonstrate the ability of d-TPP to decrease cell viability in cancer cells, but not normal cells, the viability of both MCF-7 breast cancer cells and normal human fibroblasts (hTERT-BJ1) were assessed for increasing concentrations of d-TPP (from 50 nM to 1 μM), and over different time periods (from 24 hours up to 72 hours). The results are summarized in FIGS. 4A-4C. Specifically, FIG. 4A shows results after 24 hours, FIG. 4B shows results after 48 hours, and FIG. 4C shows results after 72 hours. The data show that d-TPP reduced MCF-7 cells viability in a time- and dose-dependent manner. Higher concentrations of the compound (e.g., 250 nM, 500 nM, and 1 μM) showed an early reduction in cell viability of almost 30%, evident after only 24 hours of treatment. After 72 hours of treatment, the reduction in cell viability was nearly 80% for the higher concentrations (250 nM, 500 nM, and 1 μM) and a slight (nearly 30%) but significant inhibitory action was detected also at the lower concentrations (50 nM and 100 nM). On the other hand, the cell viability of hTERT-BJ1 cells decreased only at the higher d-TPP concentrations (250 nM, 500 nM, and 1 μM), whereas the lower concentrations (50 nM and 100 nM) showed no toxicity. These results demonstrate that d-TPP can be used to selectively target cancer rather than normal cells, particularly when used at low concentrations.

Metabolic flux analysis shows that d-TPP blocks ATP production and activates glycolysis toward the acquisition of metabolic inflexibility. Some cancer cells have the ability to switch energy sources from OXPHOS to glycolysis. This seemingly intrinsic ability to flexibly shift from one fuel source to another, according to the local availability, is a pre-requisite for abnormal cell proliferation, survival, and dissemination at distant sites. Pharmacological and/or metabolic approaches aimed at compromising this flexibility in the energetic cancer cell machinery will negatively impact the progression of the tumor.

Figure 5A:
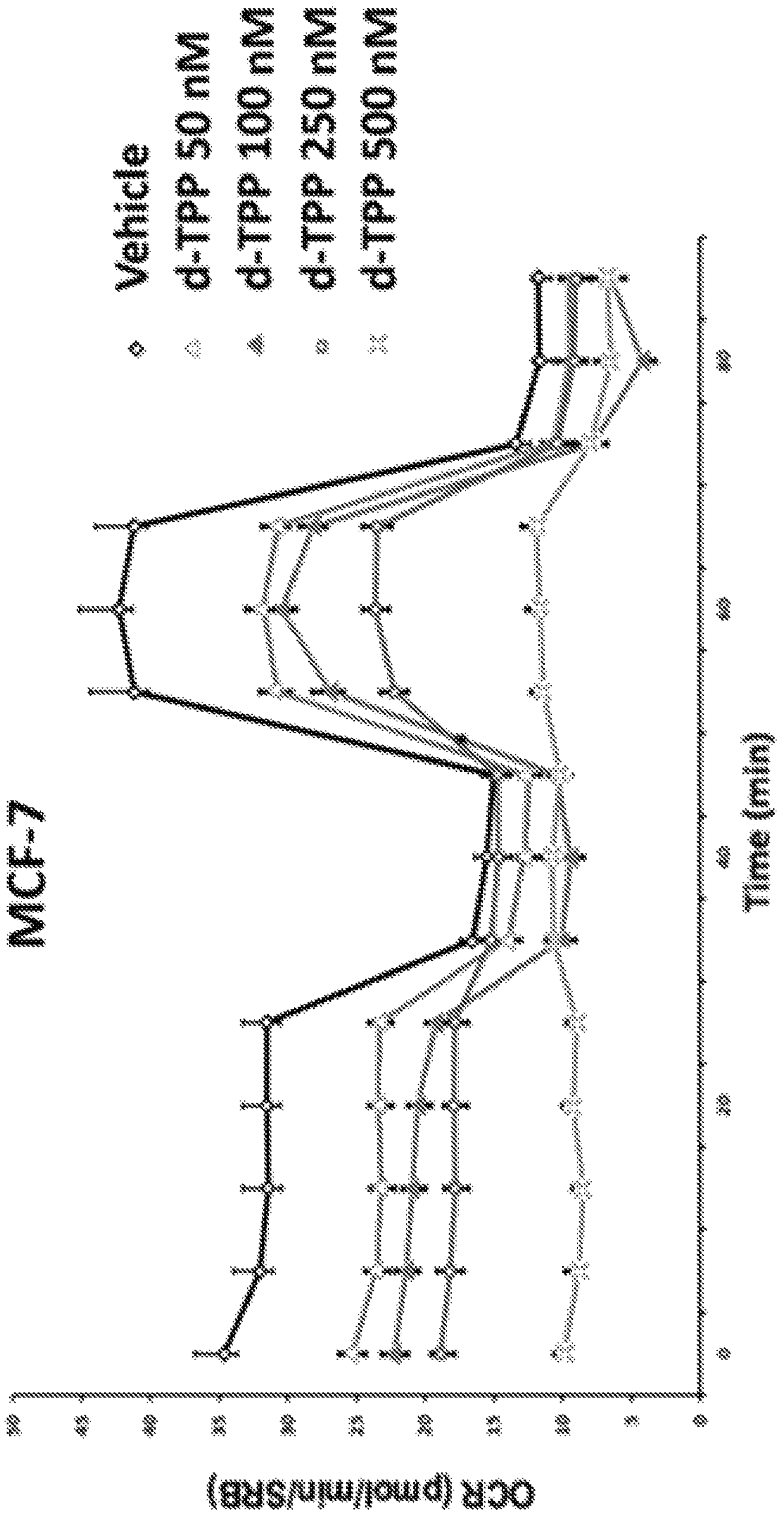
FIGS. 5A and 5B show oxygen consumption rate for MCF-7 cells treated with different concentrations of d-TPP.
Figure 5B:
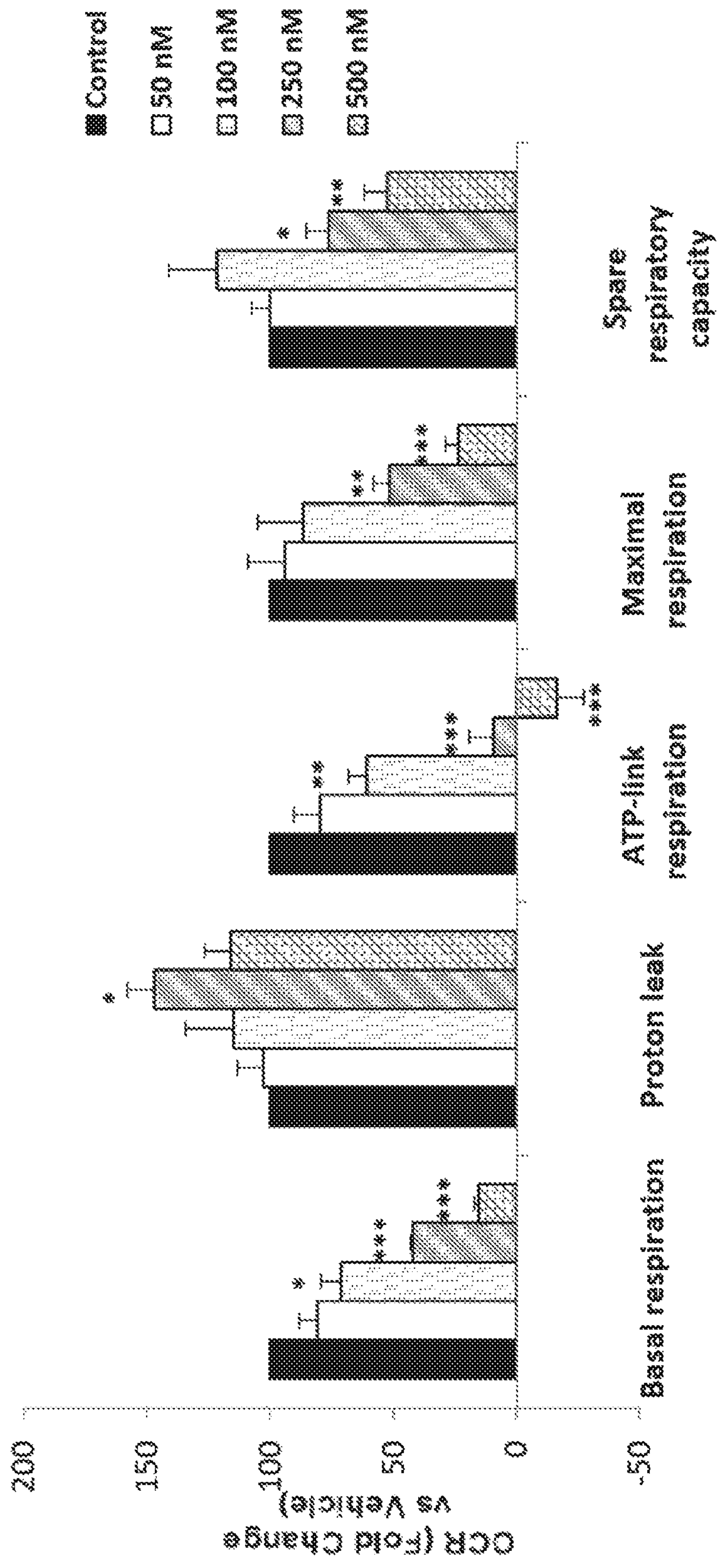

To understand the effects of d-TPP treatment on cancer cell metabolism, the inventors performed metabolic flux analysis using the Seahorse XFe96. FIGS. 5A and 5B show results of oxygen consumption rate (OCR) for MCF-7 cells treated with different concentrations of d-TPP. FIG. 5A shows OCR (pmol/min/SRB) over time, and FIG. 5B shows OCR as a fold-change versus the vehicle for basal respiration, proton leak, ATP-link respiration maximal respiration, and spare respiratory capacity. A dramatic reduction in OCR was observed in the MCF-7 cells after treatment with d-TPP at 50 nM. The reduction in OCR increased as the d-TPP concentration increased from 50 nM to 500 nM. Basal mitochondrial respiration was reduced with an IC-50 of approximately 250 nM (which is the same concentration of the drug necessary to half CSC activity); likewise, ATP levels were also dose-dependently depleted.

Figure 6A:
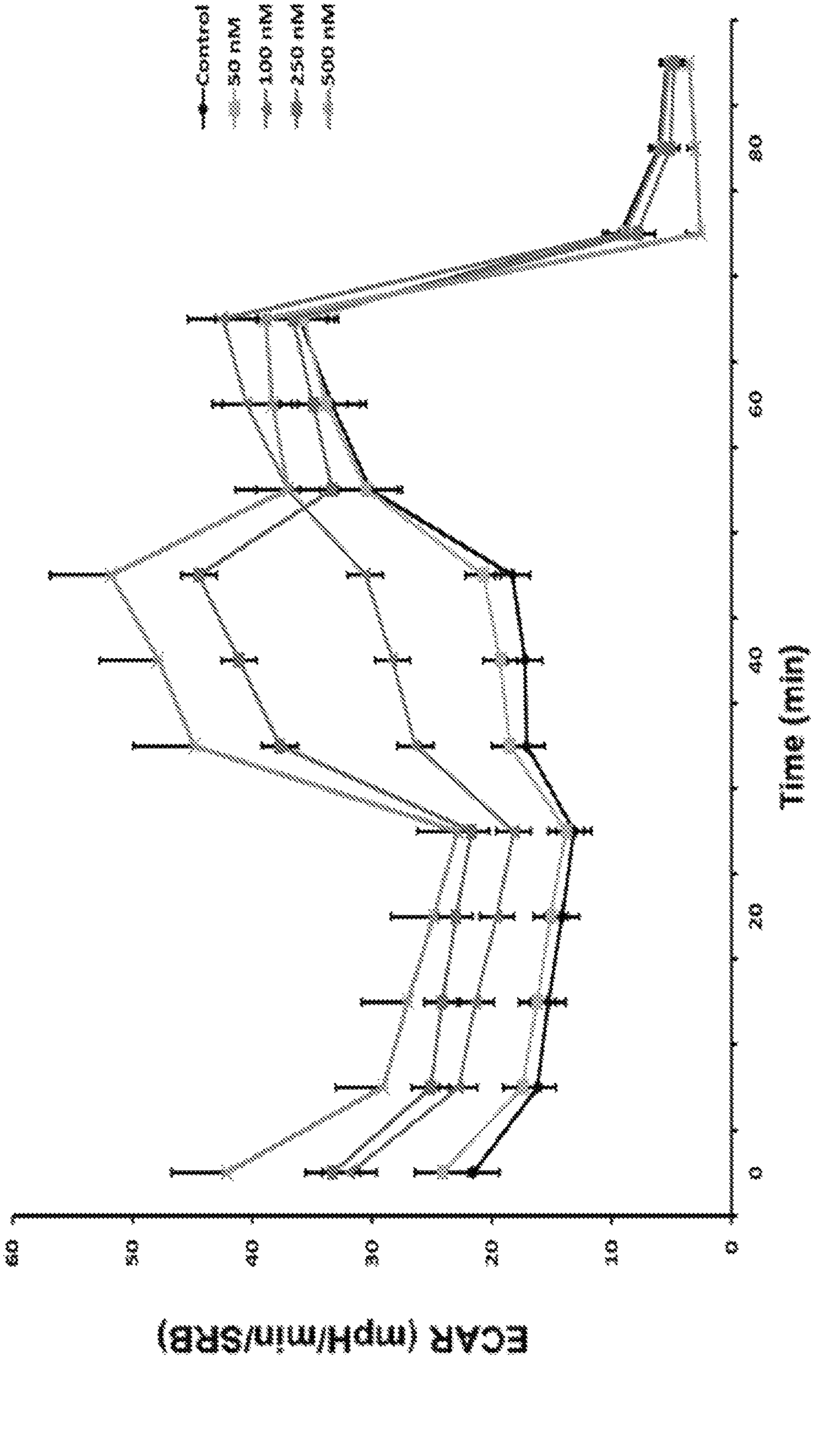
FIGS. 6A and 6B show ECAR results for concentrations of d-TPP ranging from 50 nM to 500 nM, and the vehicle-only control.
Figure 6B:
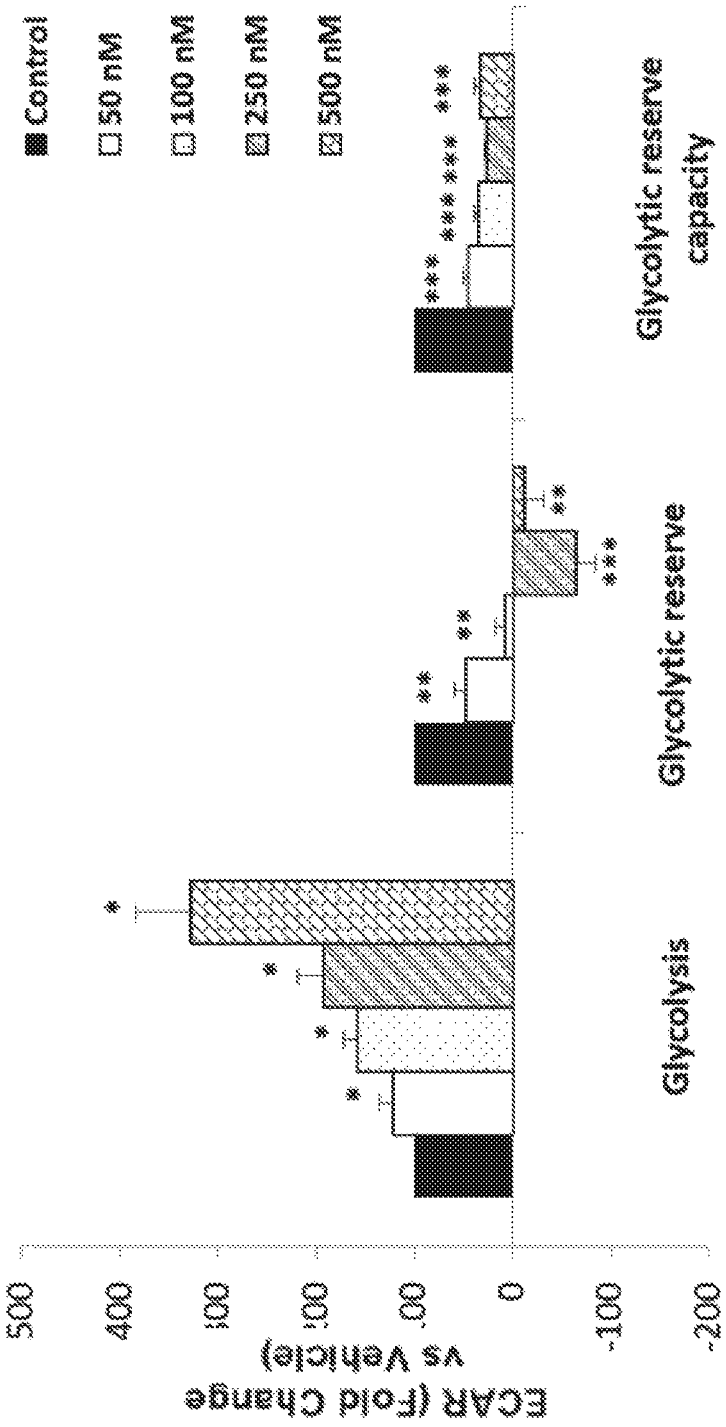

A strikingly opposite trend was observed for glycolysis, which was substantially and dose-dependently increased as indicated by the analysis of ECAR (extracellular acidification rate) in MCF-7 cells treated with d-TPP. ECAR results are shown in FIGS. 6A and 6B. In FIG. 6A, ECAR (mpH/min/SRB) is shown over time for concentrations of d-TPP ranging from 50 nM to 500 nM, and the control (vehicle-only). FIG. 6B shows ECAR as a fold-change relative to the vehicle, for glycolysis, glycolytic reserve, and glycolytic reserve capacity. As can be seen, glycolysis in MCF-7 cells increased with d-TPP treatment, in a dose-dependent manner. Altogether, these data indicate that d-TPP impairs mitochondrial function, thereafter compromising the MCF-7 cell's ability to generate ATP from oxidative phosphorylation. In order to cope with this stressful metabolic setting, cancer cells are forced to shift to a glycolytic phenotype. After this metabolic shift, the cancer cells strictly depend on glucose to fulfill their high energetic demand. In this scenario, the anti-mitochondrial effect elicited by d-TPP treatment serves as a functional metabolic synchronizer toward an obligated and inflexible glycolytic dependence.

The ability of d-TPP to inhibit mitochondrial ATP production and force CSCs to shift towards a glycolytic state, opens the door to a variety of potential treatment strategies and, in particular, therapeutic combinations. For example, d-TPP may be combined with a compound that inhibits glycolysis or OXPHOS. The timing of such combination therapies may allow the d-TPP effects to take place first, followed by the glycolysis and/or OXPHOS inhibition effects. Alternatively, d-TPP may be co-administered with the second metabolic inhibitor compound. As one example, the combination of d-TPP and Vitamin C provides a metabolic "two-hit" strategy to target metabolic vulnerabilities of CSCs. First, d-TPP inhibits ATP production and shifts the CSCs to a glycolytic profile. Second, Vitamin C inhibits glycolysis, leaving the CSCs with no metabolic option. Other inhibitors may be used in combination with d-TPP, including, for example, 2-deoxy-glucose, Doxycycline, Niclosamide, and Berberine chloride.

Figure 7B:
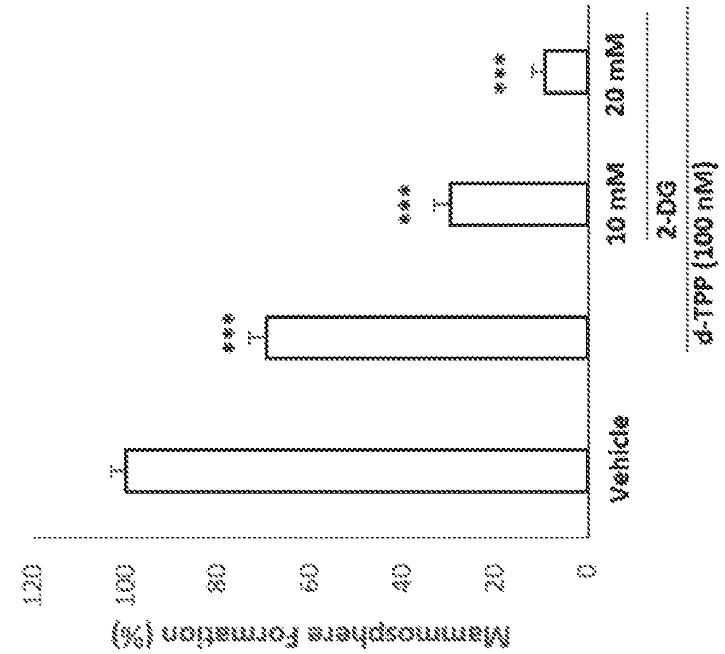
FIGS. 7A-7E show the results of the mammosphere assay on d-TPP at 100 nM in combination with second inhibitor compounds, according to some embodiments of the present approach.
Figure 7A:
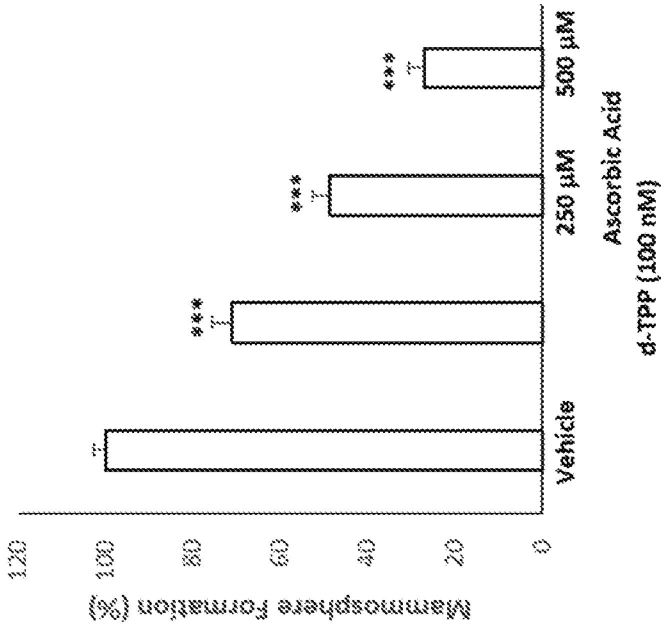

To demonstrate the effectiveness of the two-hit therapeutic approach, further evaluation was performed using the mammosphere formation assay and d-TPP at a concentration of 100 nM, the dose of the drug selectively toxic only to cancer but not normal cells. FIGS. 7A-7E show the results of the mammosphere assay for d-TPP at 100 nM, in combination with various inhibitor compounds. Starting with FIGS. 7A and 7B, natural glycolysis inhibitor Vitamin C, and synthetic glycolysis inhibitor 2-deoxy-glucose (2-DG) were included in combination with d-TPP. As can be seen in FIGS. 7A and 7B, Vitamin C and 2-DG were able to potentiate the inhibitory effect of d-TPP on CSC activity. In particular, treatment with Vitamin C inhibited the propagation of CSCs by over 50% at 250 μM and over 70% at 500 μM, when used in combination with d-TPP at 100 nM. Separately, the IC-50 for Vitamin C was 1 mM for MCF-7 CSC propagation. As can be seen, d-TPP caused a nearly 4-fold increase in CSC sensitivity to Vitamin C.

The inhibitory effect of 2-DG was observed already at the concentration of 10 mM, which resulted in a 2-fold increase in the inhibitory effect of d-TPP alone. The inhibitory effect was more dramatic at 20 mM, which almost completely suppressed CSC activity, with less than a 10% residual mammosphere formation capability.

Figure 7D:
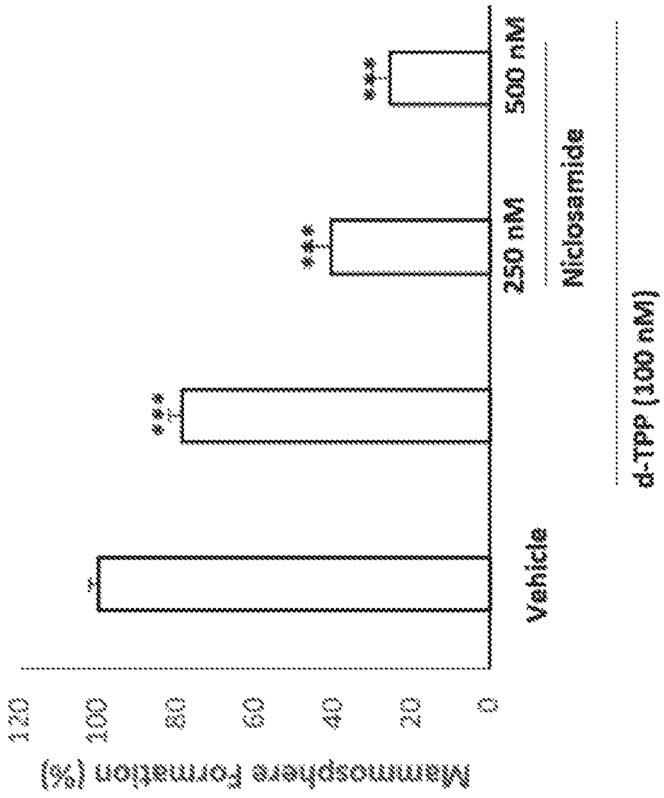
Figure 7C:
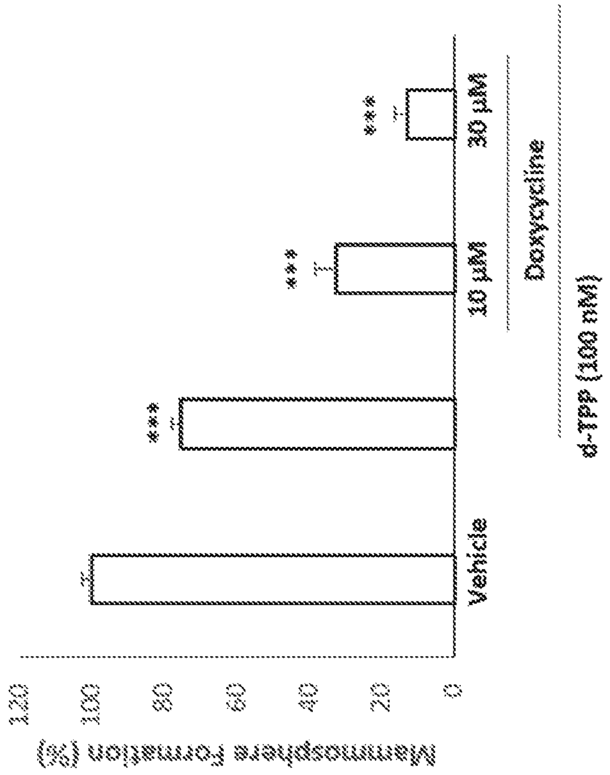
Figure 7E:
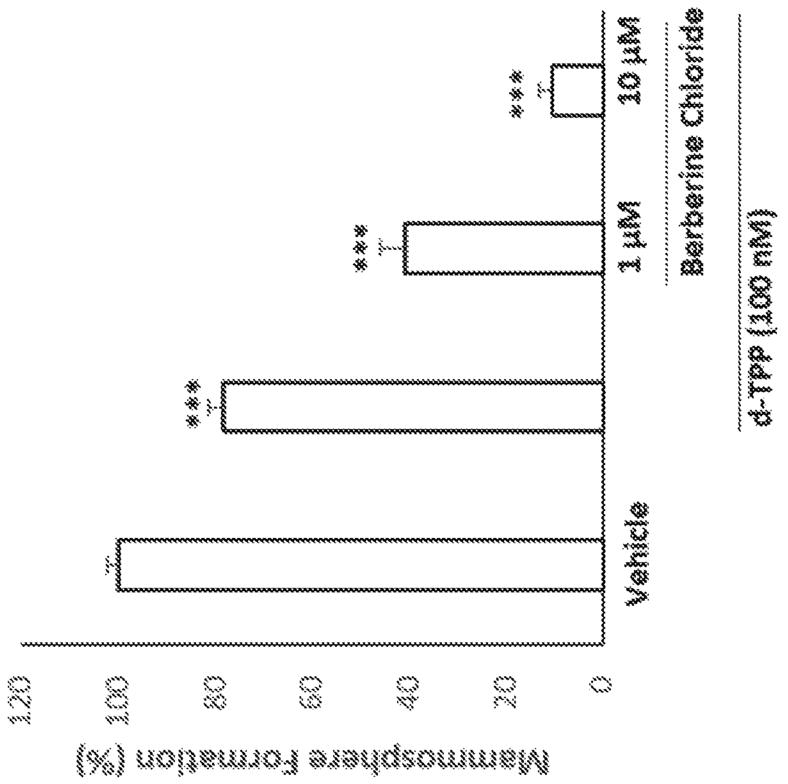
Figure 8A:
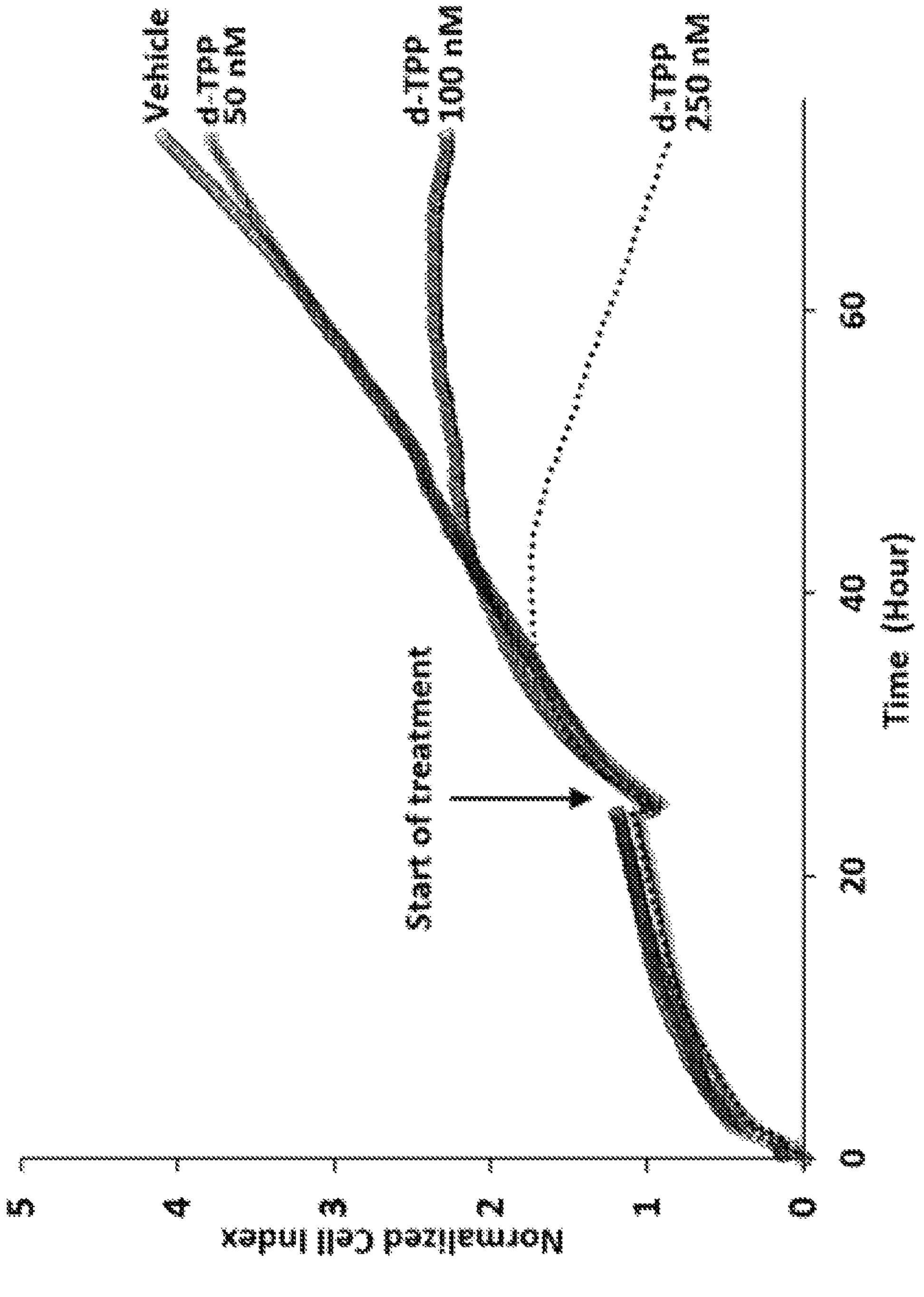
FIGS. 8A-8D show results of the xCELLigence analysis are shown in FIGS. 8A-8D. The results for the 48-hour d-TPP treatment are shown in FIGS. 8A and 8B, and FIGS. 8C and 8D show results for the 72-hour d-TPP treatment.
Figure 8B:
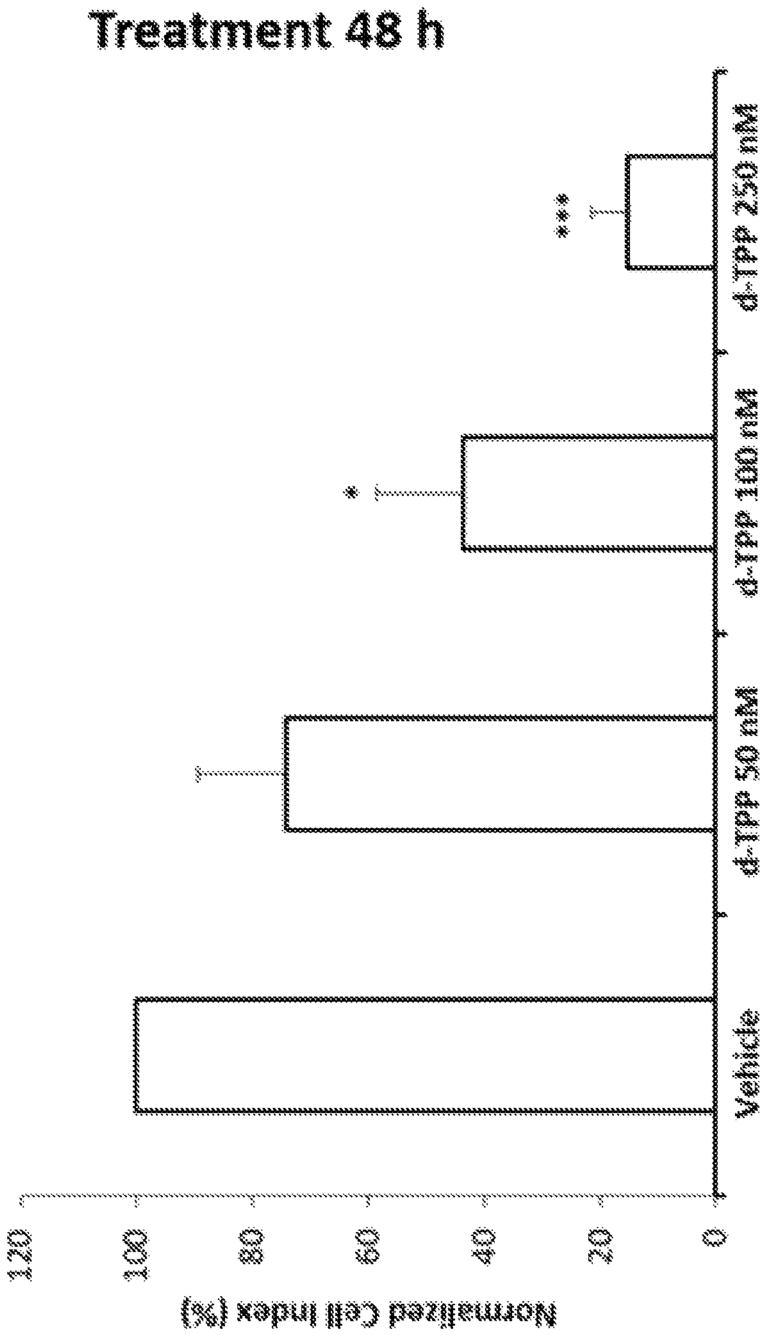
Figure 8C:
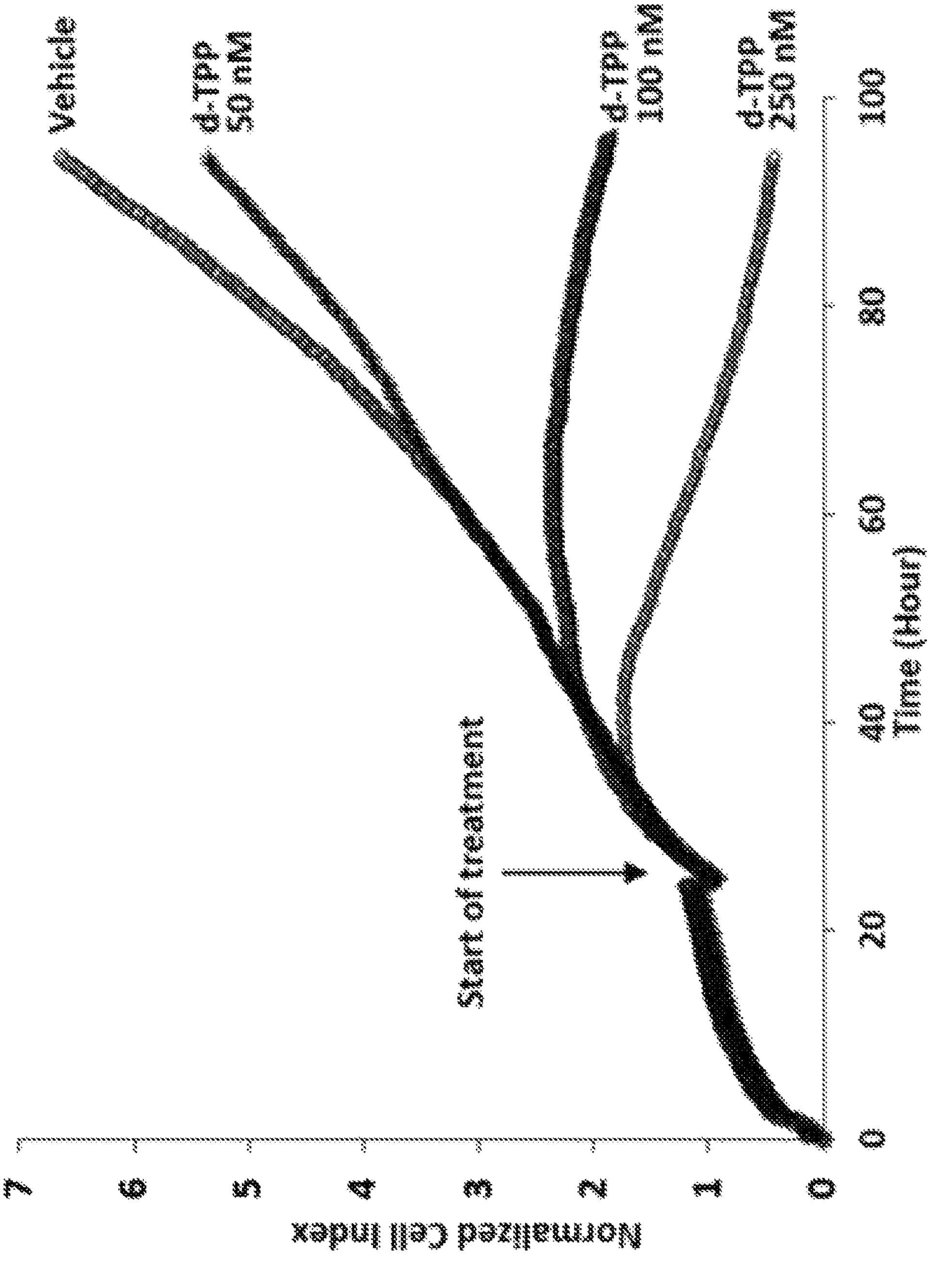
Figure 8D:
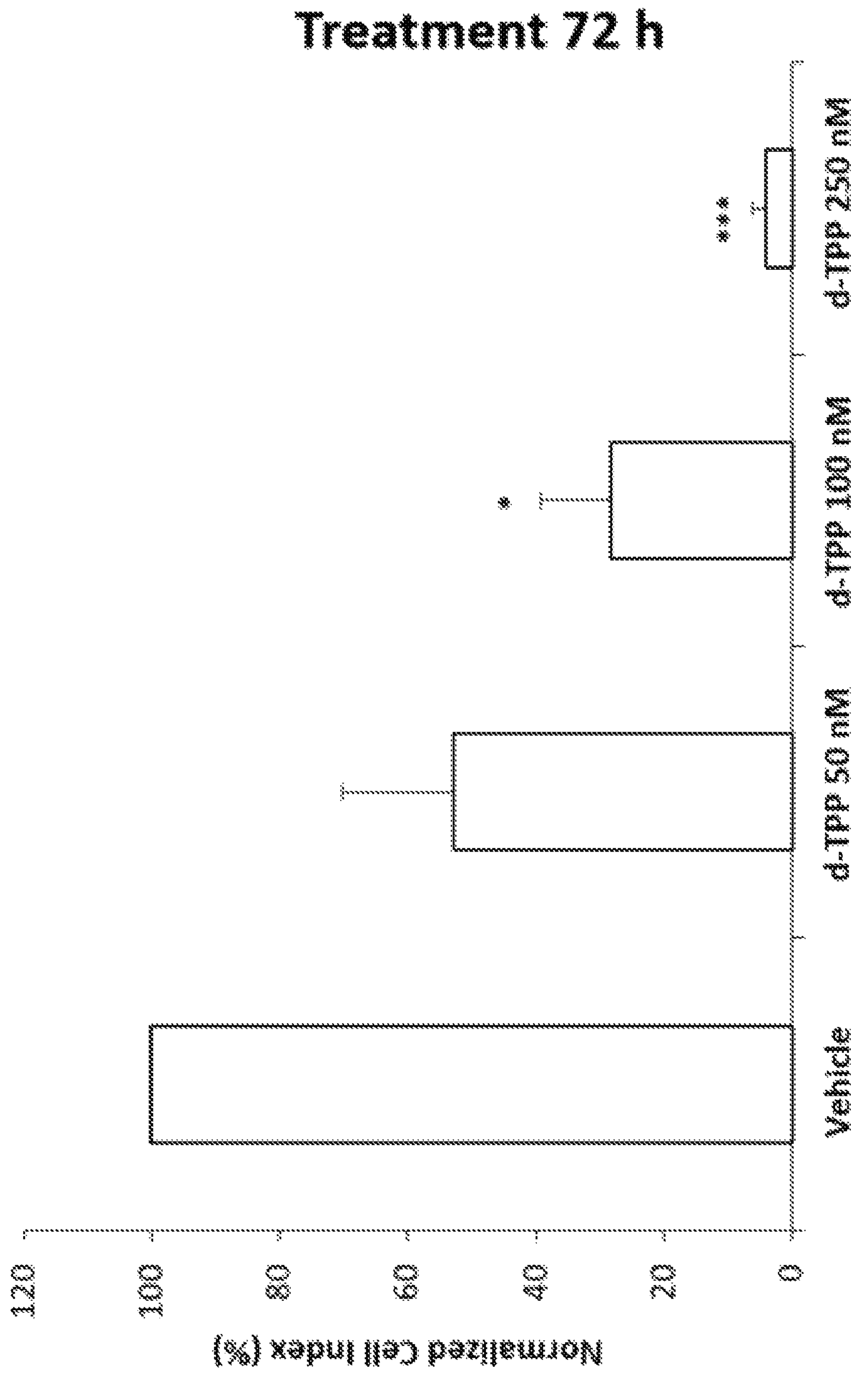

Next, FIGS. 7C-7E show results for two FDA-approved compounds, namely Doxycycline and Niclosamide, and the natural compound Berberine Chloride, in combination with d-TPP. Each of these compounds is known to behave as an OXPHOS inhibitor. This behavior is based on the understanding that in cancer cells weakened by d-TPP treatment, an additional metabolic stressor may help to eradicate the residual CSC population. Doxycycline is known to impair mitochondrial biogenesis and function. As shown in FIG. 7C, low doses of the antibiotic Doxycycline (e.g., 10 μM), were sufficient to double the efficacy of d-TPP on CSC activity. This effect was potentiated in the presence of 30 μM Doxycycline. As shown in FIG. 7D, the anti-tapeworm drug Niclosamide, which inhibits OXPHOS, increased the efficacy of d-TPP on CSC activity by nearly 2-fold at 250 nM, and by nearly 3-fold at 500 nM. FIG. 7E shows the results of natural compound and OXPHOS inhibitor Berberine chloride, in combination with d-TPP. Berberine chloride is the main alkaloid extracted from Coptidis rhizoma (Coptis chinensis Franch) and Phellodendri cortex (Phellodendron amurense Ruprecht), with known antimalarial, anti-inflammatory and antibiotic activity. Berberine chloride's action was evident already at 1 μM, which resulted in a 60% reduction. At the highest concentration tested (10 μM), Berberine chloride inhibited CSC formation by over 80%, increasing the efficacy of d-TPP by almost 5-fold.

These results demonstrate that a mitochondria-impairing agent like d-TPP compromises the normal functioning of the energetic cell machinery, thus affecting the possibility of the CSC to use alternate fuels and metabolic pathways. This effect has a negative impact on CSC biology and propagation, as well as cancer cell viability and proliferation. This negative impact leaves CSCs more vulnerable to other cancer therapies, including chemotherapy, phototherapy, and radiotherapy. CSCs treated with d-TPP will become more sensitive to the effects of other chemotherapeutics, radiation, and phototherapy. It should be appreciated that a pharmaceutically effective amount of d-TPP The xCELLigence system was used to analyze the kinetics of d-TPP action on cell proliferation of adherent MCF-7 cells. The xCELLigence system evaluates the real-time, label-free monitoring of cell health and behavior, by measuring the electrical impedance, whose magnitude is dependent on the number of cells. Real-time cell analysis was performed for 48-hour and 72-hour treatment with d-TPP, at concentrations of 50 nM, 100 nM, and 250 nM. The control was vehicle-only. The results of the xCELLigence analysis are shown in FIGS. 8A-8D. The results for the 48-hour d-TPP treatment are shown in FIGS. 8A and 8B, and FIGS. 8C and 8D show results for the 72-hour d-TPP treatment. As can be seen, the effects of d-TPP on MCF-7 cells are both dose-dependent and time-dependent, with a trend of reduced cell number after 72 h treatment with the lowest dose tested (50 nM d-TPP). At higher doses (100 nM), a main cytostatic effect was detected. Cytotoxicity was present at a d-TPP concentration of 250 nM.

Further evaluation of both efficacy and toxicity was performed on human breast tumors initiated from the MDA-MB-231 cell line in chicken embryos using the CAM Model available from Inovotion (La Tronche, France). The CAM assay showed that d-TPP inhibits both tumor growth and metastasis. For example, at a 25 sM concentration, d-TPP treatment led to a ~40% inhibition of tumor growth, and a ~75% inhibition of metastasis. With respect to the CAM assay, fertilized eggs were incubated at 37.5° C. with 50% relative humidity for 9 days. The graft was dropped into each egg through a small hole drilled through the eggshell into the air sac, and a 1 $cm^2$ window cut in the eggshell above the CAM. This grafting process was used for each egg in a test group. Because the grafting process is an invasive surgical act, some death is expected to occur during hours after the tumor graft. For the data reported herein, at least 10 eggs per test group were successfully grafted.

Figure 9:
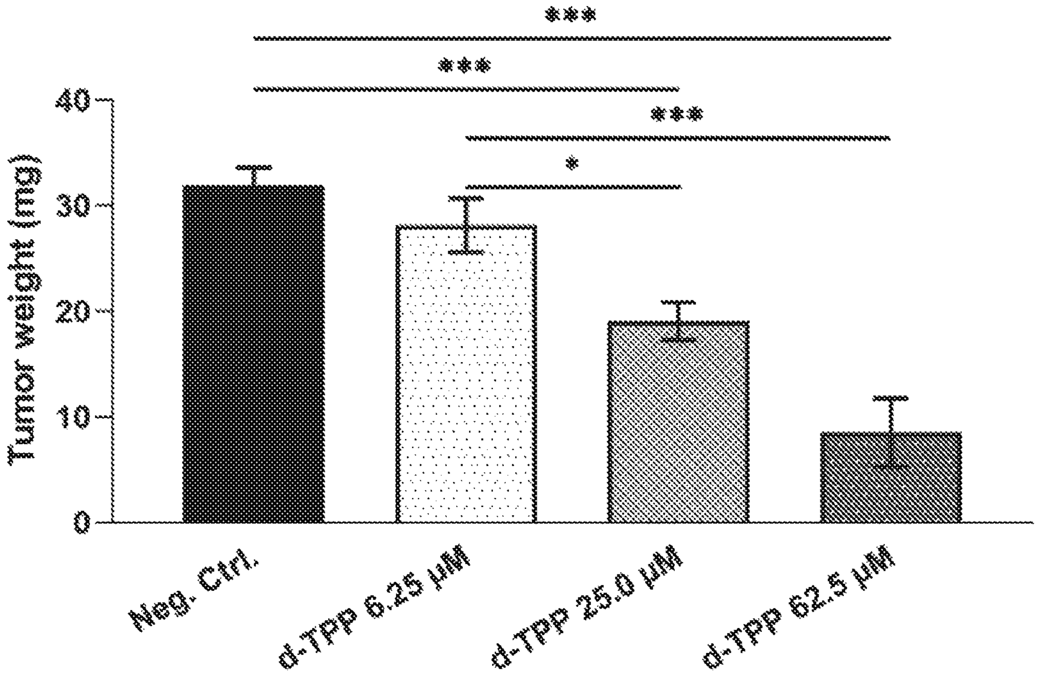
FIG. 9 shows the results of tumor weights from the CAM assay for different treatment groups.

The MDA-MB-231 tumor cell line was cultivated in DMEM medium supplemented with 10% FBS and 1% penicillin/streptomycin. After the 9-day incubation period, cells were detached with trypsin, washed with complete medium, and suspended in a graft medium. An inoculum of $1.10^6$ cells was added onto the CAM of each egg, and then eggs were randomized into test groups. Tumors were detectable within one day of the graft. The negative control group was a 0.125% DMSO in PBS, and d-TPP groups for concentrations of 6.25 μM, 25.0 mM, and 62.5 mM, were evaluated. Each egg in a group was treated 8 times per day. After 8 days of treatments, tumor growth was quantitatively evaluated. The upper portion of the CAM (with the tumor) was removed, washed in a PBS buffer, and then directly transferred in PFA for a 48-hour fixation. Tumors were then carefully cut away from normal CAM tissue and weighed. The mean values of tumor weights (in mg) are shown in FIG. 9. For all quantitative data relating to the chicken egg evaluation, a one-way ANOVA (with post-tests between each couple of groups) was performed with the specialized computer software Prism® (GraphPad Software). For all analyses, statistical difference between groups is made visible on graphs by the presence of stars with the following meaning: no asterisk means $p>0.05$; * means $0.5\geq p>0.01$;  means $0.01\geq p>0.001$; and * means $0.001\geq p$. As can be seen in FIG. 9, d-TPP significantly inhibited the tumor growth at the medium (25.0 μM) and the high (62.5 μM) doses compared to the negative control. Consistent with the evaluations described above, the d-TPP tumor growth inhibition effect was dose-dependent.

Figure 10:
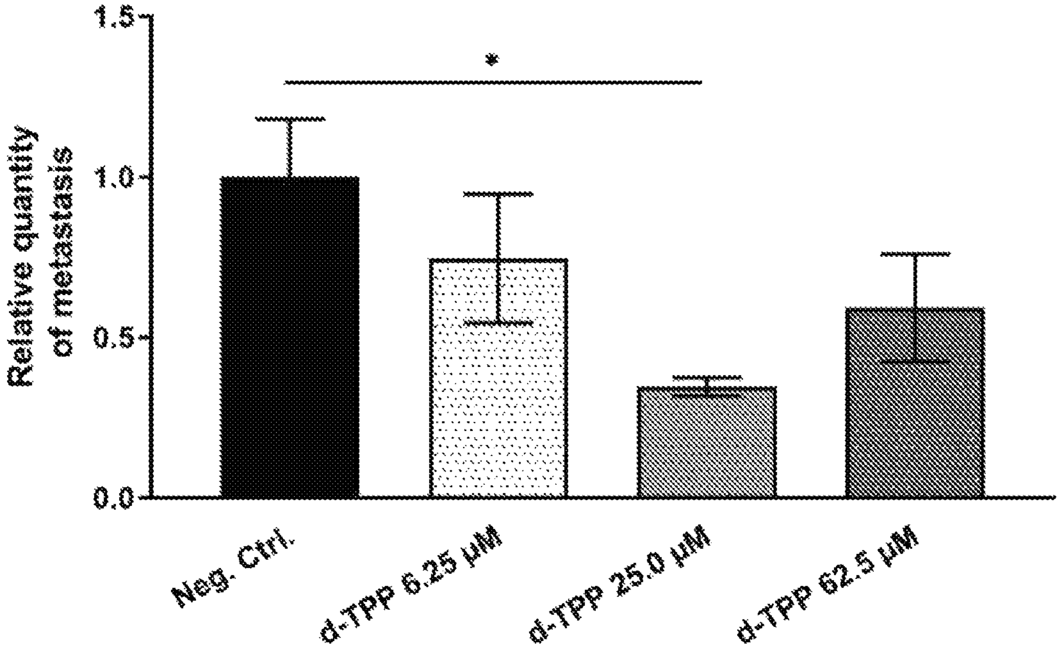
FIG. 10 shows the metastasis invasion results from the CAM assay for different treatment groups.

Metastatic invasion was also quantitatively evaluated. A 1 $cm^2$ portion of the lower CAM was collected to evaluate the number of metastatic cells in 8 samples per group (n=8). Genomic DNA was extracted from the CAM using a commercial kit, and analyzed by qPCR with specific primers for Human Alu sequences. Calculation of Cq for each sample, mean Cq and relative amounts of metastases for each group were directly managed by the Bio-Rad® CFX Maestro software. According to the Real-Time PCR Data Markup Language (RDML) data standard (http://www.rdml.org), Cq is defined as the cycle at which the curvature of the amplification curve is maximal (fractional PCR cycles). Cq is taken in the exponential phase where the qPCR curve is linear. It is the basic result of qPCR: lower Cq values mean higher initial copy numbers of the target gene. When PCR efficiency is 100%, a difference of 1 cycle between 2 reactions means that there is 2 times more copies of the gene in the reaction that has the lower Cq value than in the reaction that has the higher Cq value. FIG. 10 shows the metastatic invasion results, measured by qPCR for Alu sequences in the lower CAM. A metastasis regression can be seen after the treatment with d-TPP at the medium dose, compared to the negative control. For the group treated at the high dose, the statistical evaluation was performed using only 3 samples surviving in the group, which impacted the statistical analysis.

Figure 11:
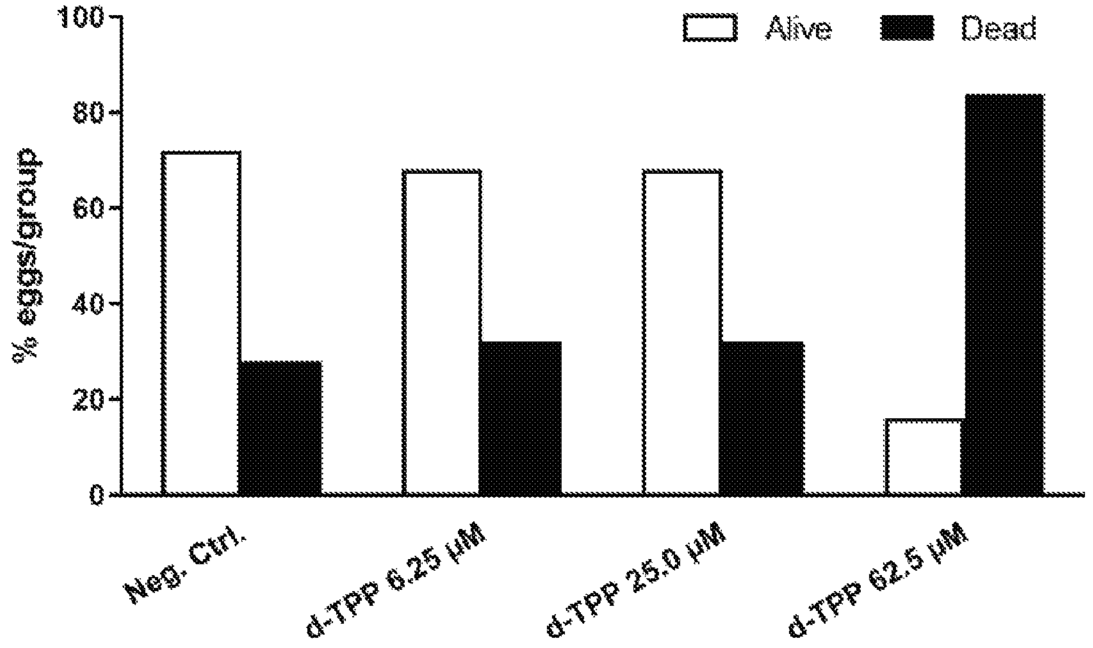
FIG. 11 shows the embryo survival from the CAM assay for different treatment groups.
Figure 12:
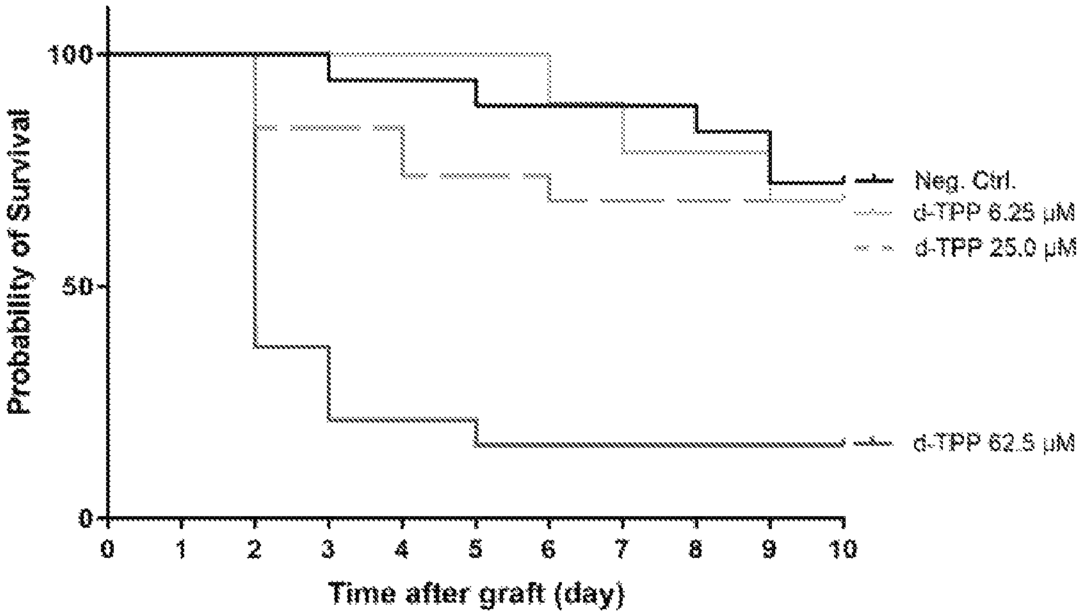
FIG. 12 is a Kaplan-Meyer curve showing the survival rates from the CAM assay for different treatment groups.

Embryonic tolerability of the d-TPP treatments were also quantitatively evaluated. Embryonic viability was checked daily following grating and during treatment. The number of dead embryos was also counted on the final day, to evaluate treatment-induced embryo toxicity. FIG. 11 shows the percentage of alive and dead embryos in each group described herein, and FIG. 12 is a Kaplan-Meyer curve showing the survival rate (from graft day to collection day). It can be seen that d-TPP did not exhibit toxicity at the medium and low doses (note that some mortality occurred in the negative control, as expected). However, the higher does resulted in mortality. It should be appreciated by those having an ordinary level of skill in the art that toxicity should be analyzed for establishing a dosing regimen. However, the results demonstrate that the tumor growth inhibition and metastasis inhibition effects of d-TPP are present at concentrations well below the toxic threshold.

The data herein presented further validate the use of a metabolic "two-hit" approach to manipulate cancer metabolism, turning the metabolic plasticity of CSCs into an obligated metabolic inflexibility, which would be used to allow a more efficient CSC suppression. The potential of d-TPP to act as a safe driver of such metabolic shift paves the way for further investigating the role of this compound in cancer biology and energetics, however further studies are warranted to support the use of TPP-based compounds in combination with other metabolic inhibitors as an add-on to conventional chemotherapy. It should be appreciated that similar effects are expected for other A-TPP compounds having saturated, linear alkyl chains with about 9 to about 18 carbons.

As an active compound, A-TPP compounds having saturated, linear alkyl chains with about 9 to about 18 carbons, such as d-TPP, may be used as a therapeutic agent for targeting cancer cells, including CSCs and circulating tumor cells, thereby treating and eradicating the cancer, preventing or reducing the likelihood of tumor recurrence, and preventing or reducing the likelihood of metastasis. Also, d-TPP may be used as an active compound for shifting cancer cells to a glycolytic state, sensitizing cancer cells to chemotherapy, radiotherapy, and phototherapy, and reducing cancer cell resistance to other pharmaceutical agents, such as Doxycycline.

With respect to the active compounds, the demonstrative second inhibitor compounds are available in various forms in the art. For A-TPP compounds such as d-TPP, the active compound can be administered orally as a solid or as a liquid. In some embodiments, d-TPP can be administered intramuscularly, intravenously, or by inhalation as a solution, suspension, or emulsion. In some embodiments, d-TPP (which, for the avoidance of doubt, includes salts thereof) can be administered by inhalation, intravenously, or intramuscularly as a liposomal suspension. When administered through inhalation the active compound or salt can be in the form of a plurality of solid particles or droplets having any desired particle size, and for example, from about 0.001, 0.01, 0.1, or 0.5 microns, to about 5, 10, 20 or more microns, and optionally from about 1 to about 2 microns. It should be appreciated that the particular form of administration may vary, and that parameters outside of the scope of this disclosure (e.g., manufacturing, transportation, storage, shelf life, etc.) may be determinative of the common forms and concentrations of d-TPP.

Pharmaceutical compositions of the present approach include d-TPP (including salts thereof) as an active compound, in any pharmaceutically acceptable carrier. If a solution is desired, water may be the carrier of choice for water-soluble compounds or salts. With respect to water solubility, organic vehicles, such as glycerol, propylene glycol, polyethylene glycol, or mixtures thereof, can be suitable. Additionally, methods of increasing water solubility may be used without departing from the present approach. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized. Embodiments including a second inhibitor compound, such as a glycolysis inhibitor or an OXPHOS inhibitor, may co-administer a form of the second inhibitor available in the art. The present approach is not intended to be limited to a particular form of administration, unless otherwise stated.

In addition to the active compound(s), pharmaceutical formulations of the present approach can contain other additives known in the art. For example, some embodiments may include pH-adjusting agents, such as acids (e.g., hydrochloric acid), and bases or buffers (e.g., sodium acetate, sodium borate, sodium citrate, sodium gluconate, sodium lactate, and sodium phosphate). Some embodiments may include antimicrobial preservatives, such as methylparaben, propylparaben, and benzyl alcohol. An antimicrobial preservative is often included when the formulation is placed in a vial designed for multi-dose use. The pharmaceutical formulations described herein can be lyophilized using techniques well known in the art.

In embodiments involving oral administration of an active compound, the pharmaceutical composition can take the form of capsules, tablets, pills, powders, solutions, suspensions, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc may be included for tableting purposes. Solid compositions of a similar type may be employed as fillers in soft and hard-filled gelatin capsules. Materials in this connection also include lactose or milk sugar, as well as high molecular weight polyethylene glycols. When aqueous suspensions and/or elixirs are desired for oral administration, the compounds of the presently disclosed subject matter can be combined with various sweetening agents, flavoring agents, coloring agents, emulsifying agents and/or suspending agents, as well as such diluents as water, ethanol, propylene glycol, glycerin and various like combinations thereof. In embodiments having d-TPP with a second inhibitor compound, the second inhibitor compound may be administered in a separate form, without limitation to the form of the d-TPP compound.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

With respect to pharmaceutical compositions, the pharmaceutically effective amount of an active compound described herein will be determined by the health care practitioner, and will depend on the condition, size and age of the patient, as well as the route of delivery. In one non-limited embodiment, a dosage from about 0.1 to about 200 mg/kg has therapeutic efficacy, wherein the weight ratio is the weight of the active compound, including the cases where a salt is employed, to the weight of the subject. In some embodiments, the dosage can be the amount of active compound needed to provide a serum concentration of the active compound of up to between about 1 and 5, 10, 20, 30, or 40 μM. In some embodiments, a dosage from about 1 mg/kg to about 10, and in some embodiments about 10 mg/kg to about 50 mg/kg, can be employed for oral administration. Typically, a dosage from about 0.5 mg/kg to 5 mg/kg can be employed for intramuscular injection. In some embodiments, dosages can be from about 1 μmol/kg to about 50 μmol/kg, or, optionally, between about 22 μmol/kg and about 33 μmol/kg of the compound for intravenous or oral administration. An oral dosage form can include any appropriate amount of active material, including for example from 5 mg to, 50, 100, 200, or 500 mg per tablet or other solid dosage form.

The following paragraphs describe the materials and methods employed in the experiments and data generation described above. The d-TPP bromide, Doxycycline, Ascorbic Acid, 2-Deoxy-D-glucose (2-DG), Berberine Chloride and Niclosamide were sourced from Sigma Aldrich. All compounds were dissolved in DMSO, except Ascorbic Acid and 2-deoxy-D-glucose (2-DG), which were dissolved in cell culture medium.

With respect to the cell cultures referenced herein, the MCF7 and MDA-MB-231 breast cancer cells were obtained from ATCC. Human immortalized fibroblasts (hTERT-BJ1) were sourced from Clontech, Inc. Cells were cultured in Dulbecco's modified Eagle's medium (DMEM), supplemented with 10% FBS (fetal bovine serum), 2 mM GlutaMAX, and 1% PenStrep in a 37° C. humidified atmosphere containing 5% $CO_2$ The mammosphere assay was performed as follows. A single cell suspension of MCF-7 or MDA-MB-231 cells was prepared using enzymatic (1× Trypsin-EDTA, Sigma Aldrich), and manual disaggregation (25 gauge needle). Cells were then plated at a density of 500 cells/$cm^2$ in mammosphere medium (DMEM-F12/B27/20-ng/ml EGF/PenStrep) in nonadherent conditions, in culture dishes coated with (2-hydroxyethylmethacrylate) (poly-HEMA, Sigma Aldrich), in the presence of treatments, were required. Cells were grown for 5 days and maintained in a humidified incubator at 37° C. at an atmospheric pressure in 5% (v/v) carbon dioxide/air. After 5 days for culture, spheres >50 μm were counted using an eye piece graticule, and the percentage of cells plated which formed spheres was calculated and is referred to as percentage mammosphere formation. Mammosphere assays were performed in triplicate and repeated three times independently.

The extracellular acidification rate (ECAR) and real-time oxygen consumption rate (OCR) assays for metabolic flux analysis were performed using the Seahorse Extracellular Flux (XFe-96) analyzer (Seahorse Bioscience). Briefly, 15,000 MCF-7 cells per well were seeded into XFe-96 well cell culture plates, and incubated overnight to allow attachment. Cells were then treated with increasing concentrations of d-TPP (50 nM÷500 nM) for 24 hours. Vehicle alone (DMSO) control cells were processed in parallel. Then, cells were washed in pre-warmed XF assay media (or for OCR measurement, XF assay media supplemented with 10 mM glucose, 1 mM Pyruvate, 2 mM L-glutamine and adjusted at 7.4 pH). Cells were then maintained in 175 μL/well of XF assay media at 37° C., in a non-$CO_2$ incubator for 1 hour. During the incubation time, 5 μL of 80 mM glucose, 9 μM oligomycin, and 1 M 2-deoxyglucose (for ECAR measurement) or 10 μM oligomycin, 9 μM FCCP, 10 μM Rotenone, 10 μM antimycin A (for OCR measurement), were loaded in XF assay media into the injection ports in the XFe-96 sensor cartridge. Data set was analyzed by XFe-96 software after the measurements were normalized by protein content (SRB). All experiments were performed three times independently.

Cell viability was assessed in MCF-7 and hTERT-BJ1 cells by sulphorhodamine (SRB) assay, based on the measurement of cellular protein content. After treatment with d-TPP (50 nM÷1 μM) for 24, 48 or 72 hours, cells were fixed with 10% trichloroacetic acid (TCA) for 1 hour in cold room, and dried overnight at room temperature. Then, cells were incubated with SRB for 15 min, washed twice with 1% acetic acid, and air dried for at least 1 hour. Finally, the protein-bound dye was dissolved in 10 mM Tris pH 8.8 solution and read using a plate reader at 540 nm.

The xCELLigence Real-time cell analysis (RTCA) System was sourced from ACEA Biosciences Inc. The xCELLigence RTCA system provides a useful approach for the real-time monitoring of the biological status of adherent cells, by measuring the electrical impedance, expressed as a cell index (CI) value. 5000 MCF-7 cells were seeded in a 16-well plate (E-plate). 24 hours after seeding, cells were treated with vehicle or increasing concentrations of d-TPP (from 50 nM to 250 nM) for additional 48 hours or 72 hours. RTCA was performed by measuring the cell-induced electrical impedance values, which were automatically recorded every 15 min for 96 h. This approach allows the quantification of the onset and kinetics of the cellular response. Experiments were repeated three times independently, using quadruplicate samples for each condition.

Unless otherwise stated, data disclosed herein is represented as the mean standard error of the mean (SEM), taken over ≥3 independent experiments, with ≥3 technical replicates per experiment, unless otherwise stated. Statistical significance was measured using the t-test. $p \leq 0.05$ was considered significant.

The terminology used in the description of embodiments of the present approach is for the purpose of describing particular embodiments only and is not intended to be limiting. As used in the description and the appended claims, the singular forms "a," "an" and "the" are intended to include the plural forms as well, unless the context clearly indicates otherwise. The present approach encompasses numerous alternatives, modifications, and equivalents as will become apparent from consideration of the following detailed description.

It will be understood that although the terms "first," "second," "third," "a)," "b)," and "c)," etc. may be used herein to describe various elements of the present approach, and the claims should not be limited by these terms. These terms are only used to distinguish one element of the present approach from another. Thus, a first element discussed below could be termed an element aspect, and similarly, a third without departing from the teachings of the present approach. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the present approach described herein can be used in any combination. Moreover, the present approach also contemplates that in some embodiments, any feature or combination of features described with respect to demonstrative embodiments can be excluded or omitted.

As used herein, the transitional phrase "consisting essentially of" (and grammatical variants) is to be interpreted as encompassing the recited materials or steps "and those that do not materially affect the basic and novel characteristic(s)" of the claim. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present approach, it is to be understood that the scope of the appended claims is not to be limited by particular details set forth in the above description as many apparent variations thereof are possible without departing from the spirit or scope thereof as hereinafter claimed.

What is claimed is:

1. A cancer therapy composition comprising an alkyl-triphenylphosphonium (A-TPP) compound of the formula:

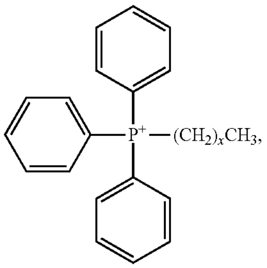

wherein 'x' is from 11 to 17, and a compound selected from the group consisting of Doxycycline, Azithromycin, Niclosamide, and Berberine chloride.

2. The composition of claim 1, wherein the A-TPP compound is dodecyl-TPP (d-TPP).

3. The composition of claim 2, further comprising a glycolysis inhibitor compound selected from the group consisting of Vitamin C and 2-deoxy-glucose.

4. The composition of claim 3, wherein the glycolysis inhibitor compound is Vitamin C.

5. The composition of claim 3, wherein the glycolysis inhibitor compound is 2-deoxy-glucose.

6. The composition of claim 1, wherein the compound is Doxycycline.

7. The composition of claim 1, wherein the compound is Niclosamide.

8. The composition of claim 1, wherein the compound is Berberine chloride.

9. A pharmaceutical composition comprising a pharmaceutically effective amount of the cancer therapy composition of claim 1.

10. The pharmaceutical composition of claim 9, further comprising a pharmaceutically effective amount of a glycolysis inhibitor compound selected from the group consisting of Vitamin C and 2-deoxy-glucose.

11. The pharmaceutical composition of claim 10, wherein compound is Doxycycline, and the glycolysis inhibitor compound is Vitamin C.

12. The pharmaceutical composition of claim 9, wherein the compound is Doxycycline.

13. The pharmaceutical composition of claim 9, wherein the compound is Azithromycin.

14. The pharmaceutical composition of claim 9, wherein the compound is Niclosamide.

15. The pharmaceutical composition of claim 9, wherein the compound is Berberine chloride.

16. The pharmaceutical composition of claim 9, wherein the pharmaceutical composition is used for at least one of treating cancer, eradicating cancer stem cells, eradicating circulating tumor cells, preventing or reducing the likelihood of tumor recurrence, preventing or reducing the likelihood of metastasis, and sensitizing a cancer to one of a chemotherapy, radiotherapy, and phototherapy.

17. A method of treating cancer, the method comprising administering to a subject a pharmaceutically effective amount of an A-TPP compound of the formula:

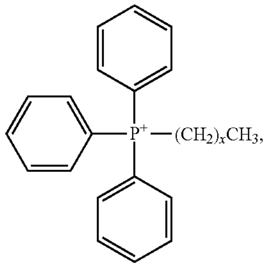

wherein 'x' is from 11 to 17, or a pharmaceutically acceptable salt thereof, and a compound selected from the group consisting of Doxycycline, Azithromycin, Niclosamide and Berberine chloride.

18. The method of claim 17, wherein the cancer is breast cancer.

19. The method of claim 17, further comprising administering a pharmaceutically effective amount of a glycolysis inhibitor selected from the group consisting of Vitamin C and 2-deoxy-glucose.

20. The method of claim 19, wherein the compound is Doxycycline.

21. The method of claim 19, wherein the A-TPP compound, or a pharmaceutically acceptable salt thereof, is administered prior to administering the glycolysis inhibitor.

22. A method of treating or preventing one of tumor recurrence and metastasis of a cancer, the method comprising administering to a subject a pharmaceutically effective amount of an A-TPP compound of the formula:

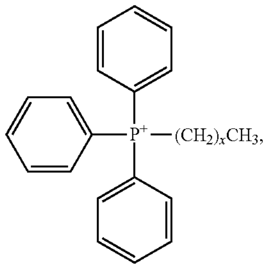

wherein 'x' is from 11 to 17, or a pharmaceutically acceptable salt thereof, and a compound selected from the group consisting of Doxycycline, Azithromycin, Niclosamide and Berberine chloride.

23. The method of claim 22, wherein the cancer is breast cancer.

24. The method of claim 22, further comprising administering a pharmaceutically effective amount of a glycolysis inhibitor selected from the group consisting of Vitamin C and 2-deoxy-glucose.

25. The method of claim 24, wherein the compound is Doxycycline.

26. The method of claim 24, wherein the A-TPP compound, or a pharmaceutically acceptable salt thereof, is administered prior to administering the glycolysis inhibitor.

27. A method of shifting a cancer to a glycolytic state, the method comprising administering to the cancer a pharmaceutically effective amount of an A-TPP compound of the formula:

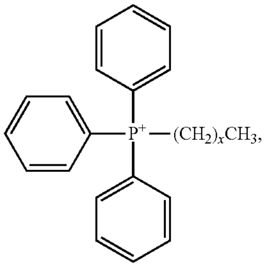

wherein 'x' is from 11 to 17, or a pharmaceutically acceptable salt thereof, and a compound selected from the group consisting of Doxycycline, Azithromycin, Niclosamide and Berberine chloride.

28. A method of increasing the effectiveness of a cancer therapy, the method comprising administering to a subject a pharmaceutically effective amount of an A-TPP compound of the formula:

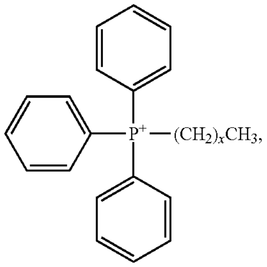

wherein 'x' is from 11 to 17 or a pharmaceutically acceptable salt thereof, and a compound selected from the group consisting of Doxycycline, Azithromycin, Niclosamide and Berberine chloride.

29. The method of claim 28, wherein the cancer therapy comprises chemotherapy.

30. A method of eradicating CSCs and circulating tumor cells in a subject, the method comprising administering to the subject:

a pharmaceutically effective amount of an A-TPP compound of the formula

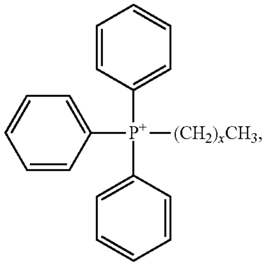

wherein 'x' is from 11 to 17, or a pharmaceutically acceptable salt thereof, and a pharmaceutically effective amount of a compound selected from the group consisting of Doxycycline, Azithromycin, Niclosamide and Berberine chloride.

* * * * *